(12) United States Patent
Choi et al.

(10) Patent No.: US 11,992,376 B2
(45) Date of Patent: May 28, 2024

(54) DENTAL RESTORATION MANUFACTURING METHOD AND MANUFACTURING SYSTEM, AND GENERAL-PURPOSE WAX BITE APPLIED THERETO

(71) Applicant: DIO Corporation, Busan (KR)

(72) Inventors: Byung Ho Choi, Wonju-si (KR); Seung Mi Jung, Wonju-si (KR); Jin Cheol Kim, Yangsan-si (KR); Jin Baek Kim, Busan (KR)

(73) Assignee: DIO CORPORATION, Busan (KR)

( * ) Notice: Subject to any disclaimer, the term of this patent is extended or adjusted under 35 U.S.C. 154(b) by 284 days.

(21) Appl. No.: 17/287,234

(22) PCT Filed: Jul. 17, 2019

(86) PCT No.: PCT/KR2019/008813
§ 371 (c)(1),
(2) Date: Apr. 21, 2021

(87) PCT Pub. No.: WO2020/105835
PCT Pub. Date: May 28, 2020

(65) Prior Publication Data
US 2021/0386527 A1    Dec. 16, 2021

(30) Foreign Application Priority Data

Nov. 19, 2018   (KR) .................. 10-2018-0142465
Nov. 26, 2018   (KR) .................. 10-2018-0147038
Nov. 26, 2018   (KR) .................. 10-2018-0147043

(51) Int. Cl.
*A61C 13/34* (2006.01)
*A61C 13/00* (2006.01)

(52) U.S. Cl.
CPC ...... *A61C 13/0006* (2013.01); *A61C 13/0004* (2013.01); *A61C 13/34* (2013.01)

(58) Field of Classification Search
CPC . A61C 13/0006; A61C 13/0004; A61C 13/34; A61B 6/14; A61B 6/03
See application file for complete search history.

(56) References Cited

FOREIGN PATENT DOCUMENTS

| KR | 10-2012-0060424 | 6/2012 |
| KR | 10-1797155 | 11/2017 |

(Continued)

OTHER PUBLICATIONS

PE2E_Kim_Translation.pdf (Year: 2017).*

*Primary Examiner* — Jan Christopher L Merene
*Assistant Examiner* — Luis M Ruiz Martin
(74) *Attorney, Agent, or Firm* — LEX IP MEISTER, PLLC

(57) ABSTRACT

To improve the precision of a dental restoration, the present invention provides a dental restoration manufacturing method comprising: a first step of preparing a general-purpose wax bite which is formed of paraffin wax, and which is formed to be standardized in correspondence to a preset standard dental arch profile and is arranged between a part in which implantation is to be performed and an opposite corresponding part, and which comprises a variable matching part corresponding to the part in which implantation is to be performed and being softened when heated to the temperature greater than or equal to a preset temperature, and a press protrusion part that is formed integrally with the variable matching part and protrudes to correspond to the opposite corresponding part and that is softened when heated to the temperature greater than or equal to a preset temperature; a second step of respectively acquiring, through an image capture device, a plurality of scanning images of the part in which implantation is to be performed and of the opposite corresponding part, before the general-purpose wax bite is provided and after the general-purpose wax bite is provided in a state where inner and outer surface (Continued)

parts of the heated general-purpose wax bite are corrected by occlusal pressure in consideration of an occlusal vertical dimension of a patient, and a CT image of an oral cavity occluded through the general-purpose wax bite, and transmitting the acquired images to a planning unit; a third step of generating an integrated scanning image by arranging the plurality of scanning images so as to correspond to the occlusal vertical dimension, and generating a three-dimensional planning image by allowing the integrated scanning image to be overlapped and matched with respect to a common part with the CT image; and a fourth step of generating design information about the dental restoration in consideration of the occlusal vertical dimension, on the basis of the three-dimensional planning information, and transmitting the design information about the dental restoration to a manufacturing device, thereby manufacturing a dental restoration.

8 Claims, 7 Drawing Sheets

(56) References Cited

FOREIGN PATENT DOCUMENTS

| KR | 10-2018-0047850 | 5/2018 | |
|----|----|----|----|
| KR | 10-1857951 | 5/2018 | |
| KR | 10-1862815 | 5/2018 | |
| WO | WO-2017188593 A1 * | 11/2017 | ............... A61B 5/00 |

* cited by examiner

DENTAL RESTORATION MANUFACTURING METHOD AND MANUFACTURING SYSTEM, AND GENERAL-PURPOSE WAX BITE APPLIED THERETO

TECHNICAL FIELD

The present invention relates to a method and a system for manufacturing a dental restoration and a general-purpose wax bite applied thereto, and more particularly, to a method and a system for manufacturing a dental restoration having improved precision of the dental restoration and a general-purpose wax bite applied thereto.

BACKGROUND ART

Generally, a dental restoration means artificial periodontal tissue in a mouth which artificially restores an exterior and a function by replacing a destroyed tooth. In detail, when a natural tooth is lost and left as it is, a distortion occurs in the dentition of adjoining teeth and a correspondingly matching tooth of the destroyed tooth so that deformation of a facial shape may be caused and a masticatory function is degraded so as to add discomfort to daily life. In addition, when a loss state of the natural tooth continues for a long time, the alveolar bone surrounding the destroyed tooth is absorbed into the body so that it is difficult to install artificial periodontal tissue.

Here, the dental restoration is installed in the oral cavity to restore the masticatory function and to prevent the correspondingly matching tooth or a residual tooth on a corresponding dental arch side which needs a dental restoration from being deformed or damaged. Here, the dental restoration may be provided as an artificial crown individually matched with the destroyed tooth and may be provided as a shape replacing a plurality of or overall destroyed teeth of the corresponding dental arch side. The dental restoration is manufactured using titanium or the like with no adverse reaction in the human body to replace a destroyed dental root and is fixed to an inside of the oral cavity using an implantation material (fixture) to be implanted into the alveolar bone.

Accordingly, since there is no secondary caries cause, the dental restoration may be stably used. Also, since the dental restoration has a structure substantially equal to the natural tooth, gum pain and a feeling of irritation are not present and the dental restoration is semipermanently usable with good care.

Meanwhile, in order to adequately design the dental restoration in a person to be treated and install it at an accurate position, accurate and precise oral information is necessary. To this end, oral surface information and internal tissue information such as an alveolar bone shape, bone density, and/or the like are all required. Accordingly, an image matching process of obtaining a three-dimensional external shape image and a three-dimensional image corresponding to an upper jaw and a lower jaw of a person to be treated and aligning and arranging the same corresponding to an occlusal vertical dimension is necessary.

In detail, the three-dimensional external shape image is obtained by gathering scanned pieces of information using an oral scanner along the oral cavity of the person to be treated. Here, the three-dimensional external shape image is distorted to have a curvature of teeth different from that of a real oral cavity while the scanned pieces of information are gathered. Accordingly, an operation of adjusting the distorted curvature of teeth in the three-dimensional external shape image on the basis of a three-dimensional image obtained through computerized tomography (CT) is necessary.

Also, soft tissue having low density such as a gingival portion is not substantially shown in the three-dimensional image. Accordingly, to design the dental restoration, an operation of supplementing surface information of the gingival portion on the basis of the three-dimensional external shape image is necessary.

Also, to prepare an implantation material adequate for a corresponding dental arch side of the person to be treated and to set a height of the dental restoration, the three-dimensional image may be obtained through CT while the upper jaw and the lower jaw are occluded in the vertical dimension of the person to be treated.

However, when any one dental arch of the upper and lower jaws is a full edentulous jaw or a partial edentulous jaw in which most teeth are destroyed, it is difficult to space the upper and lower jaws corresponding to the occlusal vertical dimension suitable for the person to be treated. Accordingly, to align and match the three-dimensional external shape image and the three-dimensional image corresponding to the occlusal vertical dimension, a process of precisely calculating the occlusal vertical dimension is necessary.

Also, in the case of the partial edentulous jaw or the full edentulous jaw, an amount of gums that are soft tissue is large so that the fluidity of tissue is high. Accordingly, it is difficult to clearly obtain the three-dimensional external shape image and precision of the dental restoration designed on the basis thereof is degraded.

In detail, general methods of calculating an occlusal vertical dimension of a person to be treated include a method of taking an impression and calculating an occlusal vertical dimension using a dental articulator, a method of using a dental tracer, a method of using a splint customized according to a person to be treated, and the like.

First, in the method of taking the impression and using the dental articulator, a tray is filled with an impression material, an impression of an oral cavity is taken, and an occlusal vertical dimension is calculated while an interval of a plaster model manufactured using the same is adjusted using the dental articulator. The method has a complicated process including taking the impression, manufacturing the plaster model, and the like and the occlusal vertical dimension is not directly calculated from the oral cavity of the person to be treated so that precision thereof is degraded. Also, in the method of using the dental tracer, a tracing stylus and a tracing plate are installed at an upper jaw and a lower jaw, respectively and an occlusal vertical dimension is calculated while a spaced interval is adjusted in consideration of an interjaw relation. This method has discomfort in that a person to be treated repetitively opens and closes his/her mouth while a height of the tracing stylus is adjusted to correspond to the occlusal vertical dimension.

Also, in order to precisely install the tracing plate on the upper and low jaws, it is necessary to manufacture an additional plaster model. That is, after the plaster model is manufactured, positions of the tracing plate and the tracing stylus are aligned using resin, putty, or wax. Here, there is a problem in that an excessive time is required for measuring the occlusal vertical dimension such as installing the tracing plate to which the resin, putty, or wax is attached in the oral cavity.

Also, the method of using the customized splint will be described as follows. First, an image of an impression model or an oral cavity of a person to be treated is obtained and a splint is separately designed and manufactured on the basis of the image. Subsequently, the manufactured splint is installed in the oral cavity after laminating/placing a wax rim and resin on inner and outer surfaces of the splint, respectively, so as to calculate an occlusal vertical dimension. This method has a problem in that the number of visits to a dental clinic, by the person to be treated, increases to perform an operation of manufacturing the splint, an operation of obtaining an image using the manufactured splint, and the like.

Also, since the probability that an error occurs in a process of transferring the impression model or obtained image to a manufacturer increases, the reliability of a separately manufactured splint decreases. In addition, since the splint is customized for each person to be treated, there is a problem that an overall cost and period required for tooth restoration increase.

DISCLOSURE

Technical Problem

The present invention is directed to providing a method and a system for manufacturing a dental restoration with improved precision of the dental restoration and a general-purpose wax bite applied thereto.

Technical Solution

One aspect of the present invention provides a method of manufacturing a dental restoration. The method includes a first operation of preparing a general-purpose wax bite formed of paraffin wax formed to be standardized corresponding to a preset standard dental arch profile, disposed between an implantation target portion and a matching target portion, and including a variable shape-matching portion corresponding to the implantation target portion and softened when heated to a temperature higher than or equal to a preset temperature and a pressing protrusion integrally formed with the variable shape-matching portion, protruding to correspond to the matching target portion, and softened when heated to a temperature higher than or equal to a preset temperature, a second operation of obtaining a plurality of scanned images of the implantation target portion and the matching target portion before and after installation in a state where inner and outer surface portions of the heated general-purpose wax bite are corrected by occlusal pressure in consideration of an occlusal vertical dimension of a person to be treated and a computerized tomography (CT) image of an oral cavity occluded with the general-purpose wax bite through an image capturing device and transmitting the plurality of scanned images and the CT image to a planning portion, a third operation of generating an integrated scanned image by aligning the plurality of scanned images to correspond to the occlusal vertical dimension while a three-dimensional planning image is generated by overlapping and matching the integrated scanned image with the CT image on the basis of a common part therebetween, and a fourth operation of generating design information of a dental restoration in consideration of the occlusal vertical dimension on the basis of the three-dimensional planning image while the design information of the dental restoration is transmitted to a manufacturing device so that the dental restoration is manufactured.

Another aspect of the present invention provides a dental restoration manufacturing system including a general-purpose wax bite formed to be standardized corresponding to a preset standard dental arch profile, disposed between an implantation target portion and a matching target portion, and including a variable shape-matching portion having a margin greater than a width of a standard gingival portion corresponding to the implantation target portion and softened when heated to a temperature higher than or equal to a preset temperature and a pressing protrusion integrally formed with the variable shape-matching portion, protruding to correspond to the matching target portion, and softened when heated to a temperature higher than or equal to a preset temperature, an image capturing device configured to obtain a plurality of scanned images of the implantation target portion and the matching target portion before installing the general-purpose wax bite and after installing the general-purpose wax bite in a state of being corrected in consideration of an occlusal vertical dimension of a person to be treated by occlusal pressure and a CT image of an oral cavity occluded with the general-purpose wax bite, a planning portion configured to generate an integrated scanned image by aligning the plurality of scanned images, to generate a three-dimensional planning image by overlapping and matching the integrated scanned image with the CT image on the basis of common parts between the integrated scanned image and the CT image, and to design a dental restoration on the basis of the three-dimensional planning image, and a manufacturing device configured to manufacture the designed dental restoration.

Still another aspect of the present invention provides a general-purpose wax bite disposed between an implantation target portion and a matching target portion and formed corresponding to a preset standard dental arch profile so that a plurality of images obtained to design a dental restoration are aligned and matched in consideration of an occlusal vertical dimension of a person to be treated. The general-purpose wax bite includes a variable shape-matching portion having a margin greater than a width of a standard gingival portion corresponding to the implantation target portion and softened when heated to a temperature higher than or equal to a preset temperature and pressurized and corrected to be shape-matched with an outer surface profile of the implantation target portion and a pressing protrusion integrally formed with the variable shape-matching portion and protruding to correspond to the matching target portion while being softened when heated to a temperature higher than or equal to a preset temperature and corrected to be occluded with the matching target portion. Also, the general-purpose wax bite is formed of a paraffin wax material.

Advantageous Effects

According to the embodiment of the present invention, the following effects are provided.

First, unlike a conventional case of using a customized splint with added costs/time or a dental tracer being inconvenient to operate, a general-purpose wax bite is prepared using a ready-made article standardized with a variety of sizes. Here, since the general-purpose wax bite can have heated inner and outer surface portions and can be corrected to precisely guide an occlusal vertical dimension using a simple method of applying an occlusal pressure, ease of use can be significantly improved.

Second, the general-purpose wax bite is formed of paraffin wax to be easily deformed corresponding to a gingival portion that is soft tissue when occluded a temperature higher than or equal to a preset temperature as well as being easily cured so as to be capable of precisely guiding an occlusal vertical dimension. In addition, since it is possible to correct the general-purpose wax bite and obtain each piece of image data at one time when a person to be treated visits a dental clinic once, an overall period and cost of tooth restoration can be significantly reduced.

Third, an unnecessary image part is deleted from three-dimensional surface information of the general-purpose wax bite and is swapped so as to expose three-dimensional surface information of a shape-matching correction portion shape-matched with an outer surface profile of an implantation target portion. As such, since image information for designing a dental restoration is obtained using the above simple method, an image processing procedure can be simplified as well as significantly improving precision.

Fourth, concordance rates between image units of preset comparative areas of a first scanned image and a second scanned image and those of a corresponding area of a third scanned image are calculated and compared. Here, when the concordance rate is higher than or equal to a preset setting value, since the first, second, and third scanned images are automatically swapped to be aligned and overlapped, an image processing process can be simplified and a processing period may be significantly reduced.

Fifth, even when a degree of shape-matching between the first scanned image and the second scanned image is low, the degree of shape-matching can be compensated for with a fourth scanned image. That is, three-dimensional surface information of an implantation target portion that is an edentulous jaw is swapped to be aligned at an accurate position corresponding to the occlusal vertical dimension using the fourth scanned image including all common parts corresponding to respective images. Accordingly, reliability of a finally generated three-dimensional planning image can be significantly improved.

BEST MODE FOR INVENTION

Exemplary embodiments of the present invention will be described below in detail with reference to the attached drawings.

Modes of the Invention

Hereinafter, a method and a system for manufacturing a dental restoration and a general-purpose wax bite applied thereto according to an exemplary embodiment of the present invention will be described in detail.

Here, the present invention may be applicable to a partial edentulous jaw or full edentulous jaw which has a large amount of tooth loss on at least one side of an upper jaw and a lower jaw so that it is difficult to calculate an occlusal vertical dimension (VD).

Also, in the present invention, it may be preferably understood that an implantation target portion means a tooth jaw where a dental restoration is substantially installed and a matching target portion means a tooth occluding with the implantation target portion. Hereafter, it will be described and illustrated that the implantation target portion includes an upper jaw of an oral cavity or an impression model prepared corresponding to the upper jaw, and the matching target portion includes a lower jaw of the oral cavity or an impression model prepared corresponding to the lower jaw. However, in the present invention, the implantation target portion may include a lower jaw or an impression model prepared corresponding to the lower jaw and the matching target portion may include an upper jaw or an impression model prepared corresponding to the upper jaw.

Also, in the present invention, a dental restoration may be preferably understood to include an artificial crown provided to separately correspond to a destroyed tooth and partial/full prosthetics including a plurality of such artificial crowns as one set. The dental restoration is fixed to an oral cavity using a dental implantation material such as a fixture and an abutment.

Here, the fixture and the abutment may be prepared as one of ready-made articles or separately manufactured, and the fixture and the abutment may be provided to have one body. Also, the dental restoration may be designed according to a person to be treated in consideration of occlusion with a matching tooth, but on a case-by-case basis, may be standardized to be designed and manufactured on the basis of standard teeth-set data prestored in a planning portion.

In addition, in the present invention, the person to be treated means a patient who needs tooth restoration, and a practitioner and a practitioner side mean a dentist and a dental clinic where an installation of a dental restoration is performed, respectively. Also, a manufacturer and a manufacturer side mean a prosthetist and a prosthetic material manufacturer manufacturing/supplying dental restorations and tools for installing the same.

Figure 1:
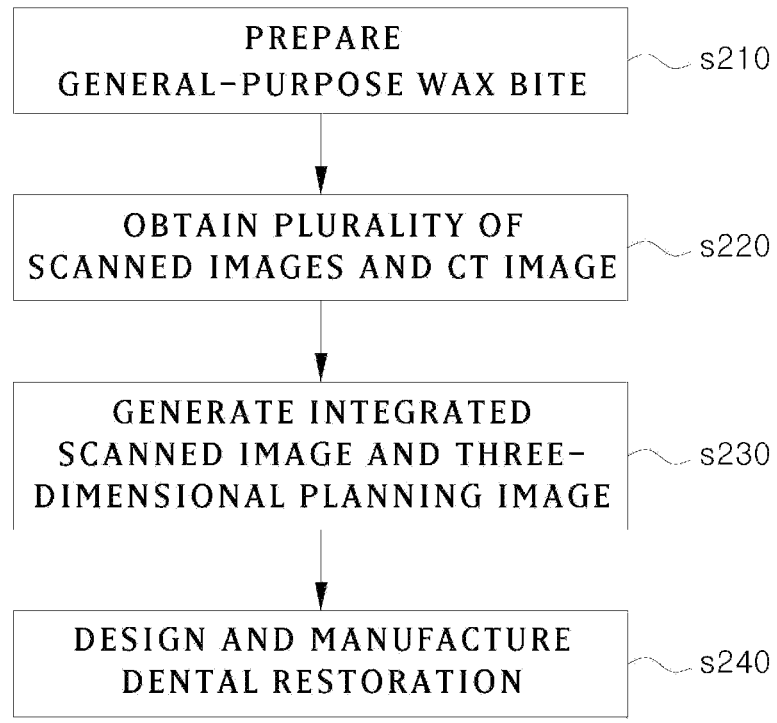
FIG. 1 is a flowchart illustrating a method of manufacturing a dental restoration according to one embodiment of the present invention.
Figure 2:
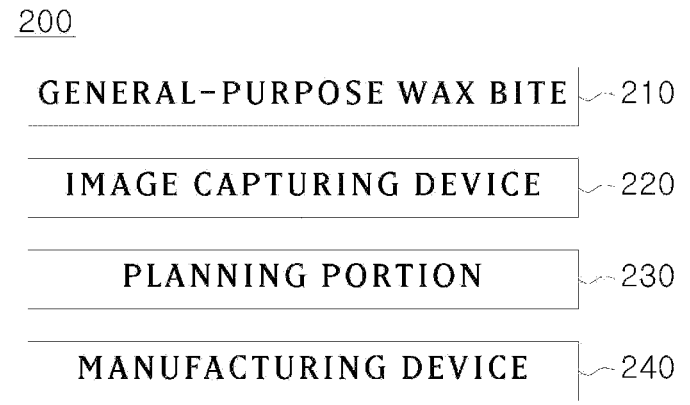
FIG. 2 is a block diagram illustrating a dental restoration manufacturing system according to one embodiment of the present invention.
Figure 3A:
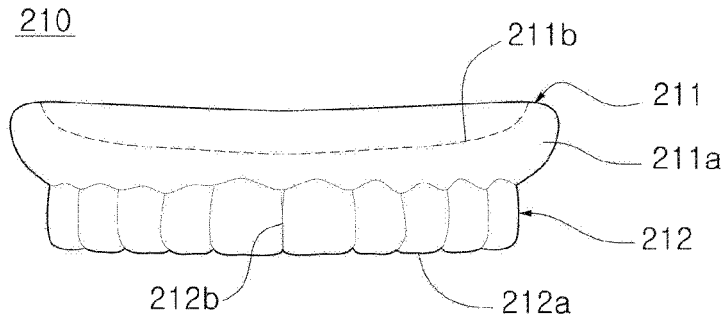
FIGS. 3A and 3B are front and plan views in which a part of general-purpose wax bite applied to the method of manufacturing a dental restoration according to one embodiment of the present invention is projected.
Figure 3B:
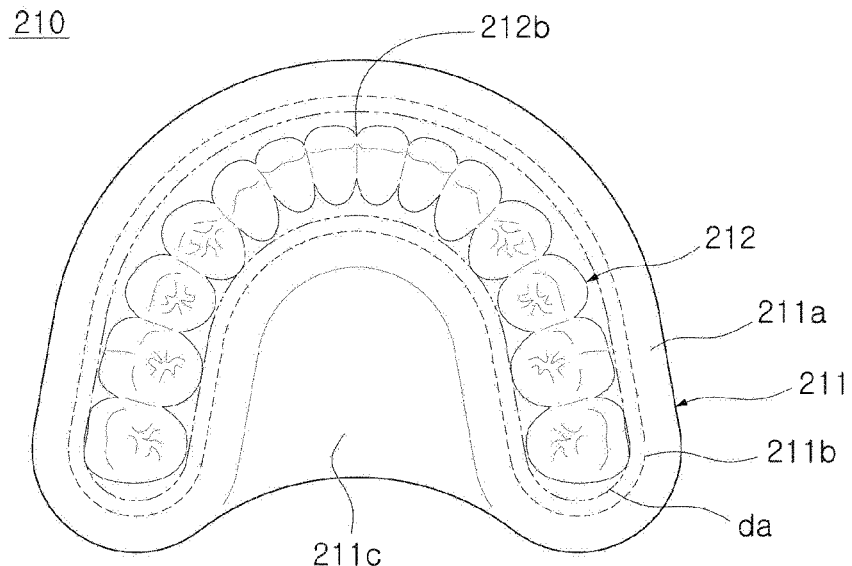
Figure 4:
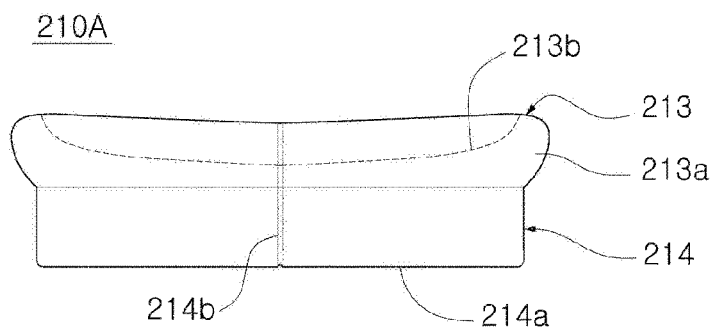
FIG. 4 is an exemplary view illustrating a modified example of the general-purpose wax bite in the method of manufacturing a dental restoration according to one embodiment of the present invention.
Figure 5:
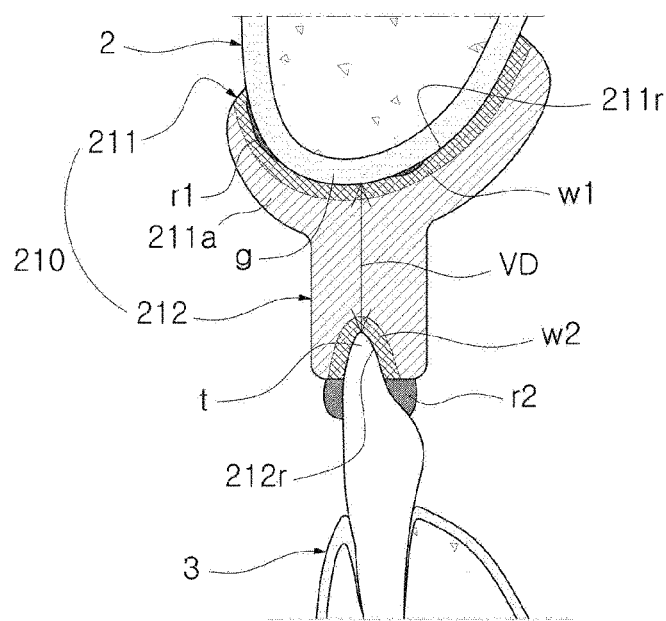
FIG. 5 is an exemplary cross-sectional view illustrating a process of correcting the general-purpose wax bite in the method of manufacturing a dental restoration according to one embodiment of the present invention.
Figure 6:
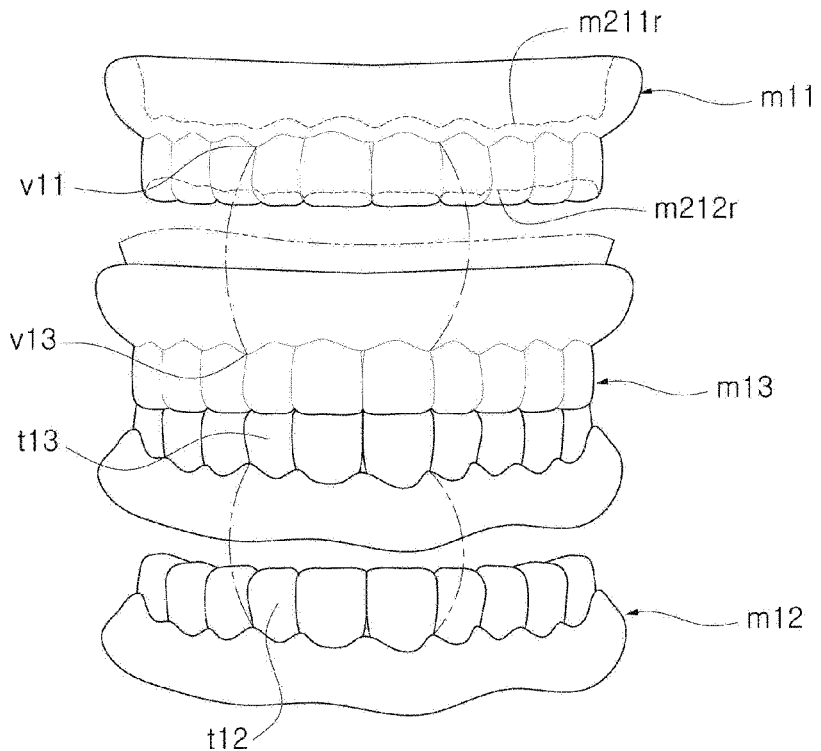
FIG. 6 is an exemplary view illustrating a process of obtaining an integrated scanned image in the method of manufacturing a dental restoration according to one embodiment of the present invention.
Figure 7A:
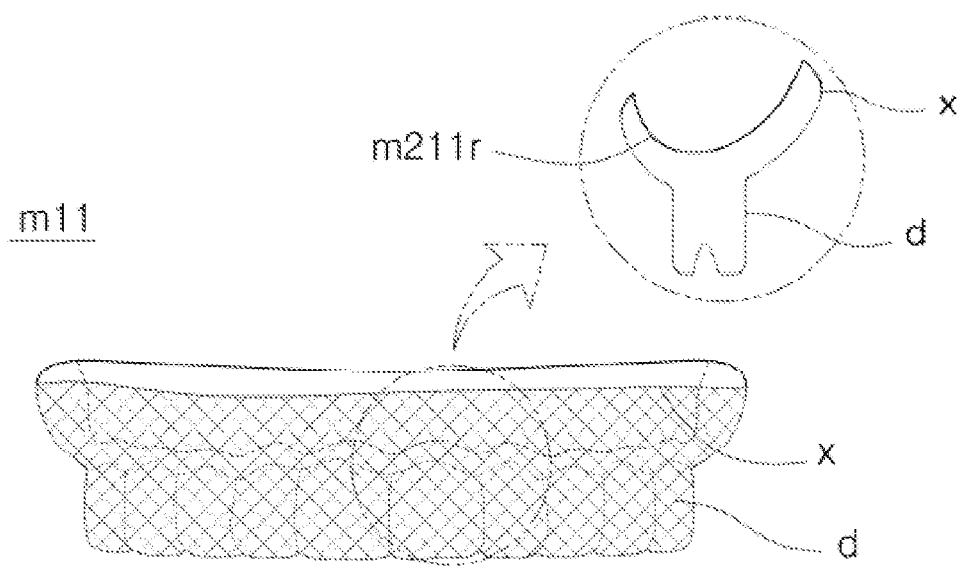
FIGS. 7A and 7B are exemplary views illustrating a process of swapping images in the method of manufacturing a dental restoration according to one embodiment of the present invention.
Figure 7B:
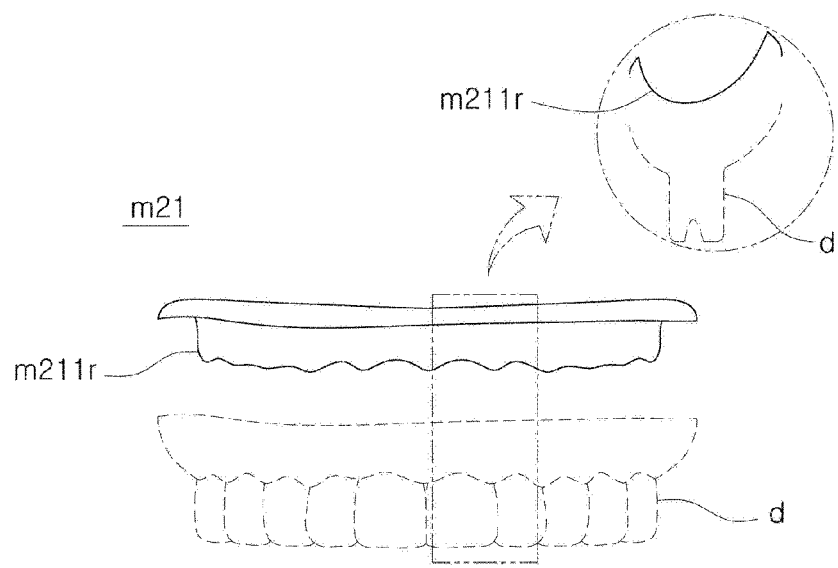
Figure 8:
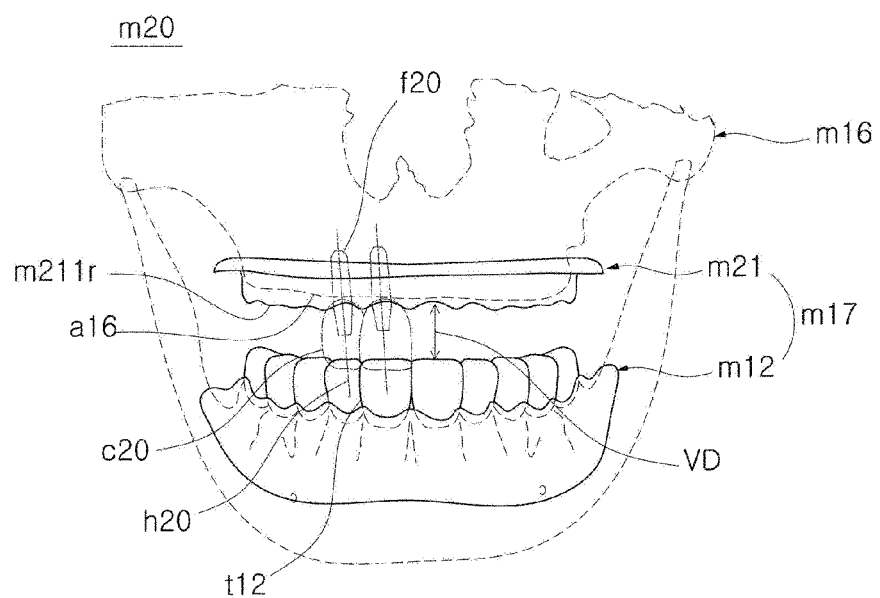
FIG. 8 is an exemplary view illustrating a three-dimensional planning image in the method of manufacturing a dental restoration according to one embodiment of the present invention.
Figure 9:
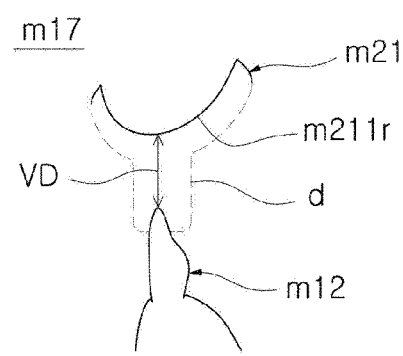
FIG. 9 is an exemplary view illustrating an integrated scanned image of an image data processing method in the method of manufacturing a dental restoration according to one embodiment of the present invention.

FIG. 1 is a flowchart illustrating a method of manufacturing a dental restoration according to one embodiment of the present invention, and FIG. 2 is a block diagram illustrating a dental restoration manufacturing system according to one embodiment of the present invention. Also, FIGS. 3A and 3B are front and plan views in which a part of general-purpose wax bite applied to the method of manufacturing a dental restoration according to one embodiment of the present invention is projected, and FIG. 4 is an exemplary view illustrating a modified example of the general-purpose wax bite in the method of manufacturing a dental restoration according to one embodiment of the present invention. Also, FIG. 5 is an exemplary cross-sectional view illustrating a process of correcting the general-purpose wax bite in the method of manufacturing a dental restoration according to one embodiment of the present invention, and FIG. 6 is an exemplary view illustrating a process of obtaining an integrated scanned image in the method of manufacturing a dental restoration according to one embodiment of the present invention. Also, FIGS. 7A and 7B are exemplary views illustrating a process of swapping images in the method of manufacturing a dental restoration according to one embodiment of the present invention, and FIG. 8 is an exemplary view illustrating a three-dimensional planning image in the method of manufacturing a dental restoration according to one embodiment of the present invention. Also, FIG. 9 is an exemplary view illustrating an integrated scanned image of an image data processing method in the method of manufacturing a dental restoration according to one embodiment of the present invention.

As shown in FIGS. 1 to 9, a method of manufacturing a dental restoration according to an exemplary embodiment of the present invention includes a series of operations of preparing a general-purpose wax bite (S210), obtaining a plurality of scanned images and a computerized tomography (CT) image (S220), generating an integrated scanned image and a three-dimensional planning image (S230), and designing and manufacturing a dental restoration (S240).

Also, the method of manufacturing a dental restoration according to the present invention may be performed using a dental restoration manufacturing system 200 including the general-purpose wax bite 210, an image capturing device 220, a planning portion 230, and a manufacturing device 240.

In detail, referring to FIG. 2, the general-purpose wax bite 210 is a tool disposed between the implantation target portion and the matching target portion so as to align and match respective pieces of image data obtained to design the dental restoration in consideration of an occlusal vertical dimension of a person to be treated.

Here, the tool disposed between the implantation target portion and the matching target portion is not limited to the general-purpose wax bite 210 and may include a variety of well-known coupling bites configured to guide an occlusal vertical dimension of a person to be treated. For example, a bite check tool such as a tray, a denture, a splint, and a wax rim may be provided as the coupling bite.

Here, the general-purpose wax bite 210 is provided as one of ready-made articles and may be formed of a material correctable so as to correspond to an occlusal vertical dimension suitable for each person to be treated. Accordingly, in a process of obtaining each piece of image data required in designing the dental restoration, a precise vertical dimension may be guided through the general-purpose wax bite 210 corrected according to the person to be treated. Here, each piece of the image data may be understood as a concept including a plurality of such scanned images and the CT image.

Also, the image capturing device 220 may be understood as including an oral scanner and a CT apparatus. In detail, the plurality of scanned images that are three-dimensional surface information on outer surfaces of the implantation target portion, the matching target portion, and the general-purpose wax bite 210 are obtained. Also, the CT image that is internal tissue information on densities, alveolar bone shapes, and the like of the upper and lower jaws is obtained using the CT apparatus.

Also, the planning portion 230 may be understood as a design device configured to design the dental restoration on the basis of respective pieces of image data which are obtained using the image capturing device 220 and prestored design information. In addition, an implantation plan for a dental implantation material such as a fixture and an abutment for fixing the dental restoration in the oral cavity may be devised through the planning portion 230. Also, the devised implantation plan may virtually simulate implantation of a dental implantation material and tooth restoration through a dental restoration on the basis of the devised implantation plan.

In addition, a surgical guide configured to guide an accurate implantation position/depth/direction of the dental implantation material through the planning portion 230 is designed. Accordingly, accuracy and precision in tooth restoration using the dental restoration may be significantly improved.

Meanwhile, the manufacturing device 240 may be understood as a three-dimensional printer, a milling device, or the like configured to manufacture real articles by three-dimensional printing or milling the dental restoration and the surgical guide to correspond to design information generated through the planning portion 230. However, the manufacturing device 240 may further include a molding device provided to correspond to designed information.

Referring to FIGS. 3A to 4, the general-purpose wax bite 210 or 210A disposed between the implantation portion and the matching target portion is provided (S210 in FIG. 1). Here, the general-purpose wax bite 210 or 210A may be formed to be standardized corresponding to a preset standard dental arch profile da, and a variable shape-matching portion 211 or 213 and a pressing protrusion 212 or 214 may be integrally formed.

In detail, the general-purpose wax bite 210 or 210A may have an overall arch shape in which an outer surface portion 212a or 214a protrudes from one matching side between the implantation target portion and the matching target portion while an inner surface portion 211b or 213b is recessed to a certain depth.

The arch shape may correspond to the standard dental arch profile da. Here, the standard dental arch profile da may be understood as a surface having a certain area corresponding to an interval between an outside and an inside of a gingival portion surrounding the alveolar bone that is a part of the implantation target portion where teeth are substantially arranged. Here, the outside of the gingival portion may be understood as a part corresponding to a labial side and a buccal side, and the inside of the gingival portion may be understood as a part corresponding to a lingual side.

The standard dental arch profile da may be standardized and calculated in consideration of anatomical deviations by age and gender.

In detail, the standard dental arch profile da may be calculated while being classified stage by stage in response to an average value representing an arch size by age and gender. Accordingly, the general-purpose wax bite 210 or 210A may be mass-produced while being classified to have preset sizes. For example, the general-purpose wax bite 210 or 210A may be provided while being provided as standardized ready-made article sets classified into six sides, that is, large/medium/small of an upper jaw side and large/medium/small of a lower jaw side.

That is, since the occlusal vertical dimension is guided using the general-purpose wax bite 210 or 210A mass-produced as ready-made articles in the present invention, a period of time consumed for calculating the occlusal vertical dimension may be reduced and an overall cost may be economically reduced while the dental restoration is designed. Accordingly, a general problem of excessive time and costs being consumed for calculating the occlusal vertical dimension using a tracer or a customized splint may be remedied.

In detail, since the tracer needs an additional impression model to be accurately installed in the oral cavity and a technician who substantially adjusts a tracing stylus is a practitioner or a manufacturer, a difference from an occlusal vertical dimension determined by a person to be treated may occur. Also, in the case of a separately customized splint, inaccurate information may be reflected due to an error in a process of repetitively transmitting/transferring information for designing the splint between the practitioner side and the manufacturer side.

On the other hand, in the present invention, since a practitioner who determines mastication sensitivity and corrects a thickness and a shape of the general-purpose wax bite 210 or 210A is actually the person to be treated on the basis thereof, an occlusal vertical dimension optimized for each person to be treated may be reflected. Accordingly, precision and accuracy of a dental restoration designed and manufactured on the basis of the accurately calculated vertical dimension may be significantly improved.

In addition, the general-purpose wax bite 210 or 210A may be a provided as a ready-made article and may be mass-produced while being standardized in a plurality of sizes to be generally applicable to oral cavities of a variety of people to be treated or impression models corresponding thereto. Accordingly, since the practitioner side provides the general-purpose wax bite 210 or 210A by size in advance to be instantaneously usable when the person to be treated visits, convenience in use may be significantly improved. Also, the number of visits to a dental clinic by the person to be treated may be substantially minimized to one time for an operation of obtaining information on the implantation target portion and the matching target portion before installing the dental restoration.

Also, the plurality of scanned images and the CT image may be obtained as soon as the general-purpose wax bite 210 or 210A is corrected to be suitable for each person to be treated. Here, since the time points of obtaining the plurality of scanned images and the CT image are substantially equal, a matching rate of respective pieces of image data may be significantly improved.

Meanwhile, the variable shape-matching portion 211 or 213 is provided on an inner surface portion side of the general-purpose wax bite 210 or 210A and may be formed to have a margin 211a or 213a which exceeds a width of a standard gingival portion corresponding to the implantation target portion. Also, the pressing protrusion 212 or 214 may be provided on an outer surface portion side of the general-purpose wax bite 210 or 210A and integrally formed with the variable shape-matching portion 211 or 213 while protruding to correspond to the matching target portion.

In addition, referring to FIGS. 3A and 3B, in the case of a partial edentulous jaw in which residual teeth are present on the implantation target portion side, an interdentium corresponding portion 212b configured to guide a cut position to cut and correct the general-purpose wax bite corresponding to a residual teeth area of the implantation target portion side may be formed.

In detail, the pressing protrusion 212 or 214 may be formed to have an arch shape corresponding to the preset standard dental arch profile da while having an outer surface corresponding to an exterior of a tooth. That is, the pressing protrusion 212 may be formed to include a masticating surface corresponding to a rear tooth shape and the interdentium corresponding portion 212b.

Here, the interdentium corresponding portion 212b may be shown in intaglio and may be used as an alignment marker that becomes an alignment reference for disposition between the implantation target portion and the matching target portion. In detail, the alignment marker may be aligned corresponding to a preset visible reference indicator on any one side of the implantation target portion and the matching target portion. Here, the visible reference indicator may be formed as an interdentium between residual teeth on a correspondingly matching side, and in some cases, the maxillary labial frenum or the mandibular labial frenum corresponding to the midline of the human body may be set as the visible reference indicator.

Also, a residual tooth region of the general-purpose wax bite 210 may be compared with a position of the residual tooth of the implantation target portion side and in the interdentium 212b and cut and deleted. Accordingly, even when the general-purpose wax bite 210 is integrally formed to correspond to the standard dental arch profile da, it may be easily cut and corrected to correspond to an oral environment.

Accordingly, when the general-purpose wax bite 210 is corrected, inner and outer surface portions may be accurately corrected to correspond to the implantation target portion and the matching target portion. Also, even when the corrected general-purpose wax bite 210 is repetitively installed/separated between and from the implantation target portion and the matching target portion, an accurate position may be uniformly guided.

Alternatively, as shown in FIG. 4, the pressing protrusion 214 may have a simply protruding shape with a cross section corresponding to the preset standard dental arch profile. In this case, a shape of the general-purpose wax bite 210 is simplified and easily manufactured so that productivity may be improved and manufacturing costs may be reduced.

Here, the alignment marker 214b may be further included in the pressing protrusion 214 and a preset outer surface of the variable shape-matching portion 213 integrally formed therewith. The alignment marker 214b may be manufactured in the displayed state when the general-purpose wax bite 210 is mass-produced, and in some cases, may be displayed by a practitioner using a tool in an operation of correcting the general-purpose wax bite 210.

Meanwhile, referring to FIGS. 3A to 4, the margin 211a or 213a may be formed to exceed a width of the standard gingival portion. Here, the width of the standard gingival portion may be understood as a standard lateral interval between an outside and an inside of the gingival portion which is calculated in consideration of anatomical deviations by age and gender. The width may be understood as a standardized lateral interval between a labial side and a lingual side of the gingival portion which is calculated in consideration of the anatomical deviations by age and gender. In addition, the width of the standard gingival portion may be understood as a width substantially corresponding to or set to be greater than the standard dental arch profile da.

Accordingly, the margin 211a or 213a may be formed to have a laterally extending area rather than the width of the standard gingival portion. Accordingly, the general-purpose wax bite 210 or 210A may be disposed to entirely surround the inside and outside of the gingival portion of the implantation target portion. Also, an inner surface 211b or 213b of the variable shape-matching portion 211 or 213 may be formed to be concave with a curvature smaller than that of a convex outer surface profile of the gingival portion of the average implantation target portion side. Accordingly, an adequate marginal volume in which the outer surface of the implantation target portion is corrected to be shape-matched may be secured while coming into overall contact with the variable shape-matching portion 211.

Meanwhile, in the present invention, since an inner surface portion 211b or 213b of the general-purpose wax bite 210 or 210A is substantially the same as the inner surface 211b or 213b of the variable shape-matching portion 211 or 213, it may be understood why they are described and illustrated with the same reference numeral. Also, since an outer surface portion 212a or 214a of the general-purpose wax bite 210 or 210A is substantially the same as the outer surface 212a or 214a of the pressing protrusion 212 or 214, it may be understood why they are described and illustrated with the same reference numeral.

Also, in the general-purpose wax bite 210 or 210A, a thickness between the inner surface 211b or 213b of the variable shape-matching portion 211 or 213 and the outer surface 212a or 214a of the pressing protrusion 212 or 214 may be formed to be greater than an average vertical dimension calculated in consideration of the anatomical deviations by age and gender. Accordingly, while the general-purpose wax bite 210 or 210A softened by heating the inner and outer surface portions is disposed between the implantation target portion and the matching target portion, an adequate marginal thickness correctable by simple occlusal pressure may be secured.

In addition, a reinforcing surface portion 211c may be further formed to support a space between both ends of the variable shape-matching portion 211 or 213 formed to have an arch shape and the pressing protrusion 212 or 214. Accordingly, even when the occlusal pressure is applied while the inner and outer surface portions of the general-purpose wax bite 210 or 210A are softened so that supporting strength is reduced, distortion or fracture may be prevented. Also, in a case of corresponding to the upper jaw side, since occlusion is corrected while the reinforcing surface portion 211c is supported by the hard palate, the general-purpose wax bite 210 or 210A may be prevented from sliding and shifting in position in occlusion. Accordingly, the corrected general-purpose wax bite 210 or 210A may be precisely corrected to accurately guide the occlusal vertical dimension. Meanwhile, referring to FIG. 5, the general-purpose wax bite 210 is provided while being standardized as a ready-made article, but is selected and used as a product having a size suitable for a person to be treated. Also, the variable shape-matching portion 211 occluded between the implantation target portion 2 and the matching target portion 3 and facing/corresponding to the implantation target portion 2 is softened when heated to a preset temperature or higher. Also, the pressing protrusion 212 facing/corresponding to the matching target portion 3 is softened when heated to a preset temperature or higher. Here, parts w1 and w2 shown in FIG. 5 may be understood as parts softened by heating.

Also, before or after each piece of the image data is obtained, the general-purpose wax bite 210 is disposed between the implantation target portion 2 and the matching target portion 3 while the inner and outer surface portions thereof are softened. Here, the inner and outer surface portions of the general-purpose wax bite 210 are heated and softened to have lower strength than the implantation target portion 2 and the matching target portion 3. Accordingly, an inner surface profile of the variable shape-matching portion 211 and an outer surface profile of the pressing protrusion 212 are deformed to correspond to outer surface profiles of the implantation target portion 2 and the matching target portion 3, respectively, by occlusal pressure. Additionally, a thickness between the variable shape-matching portion 211 and the pressing protrusion 212 is deformed to correspond to the occlusal vertical dimension VD.

In detail, the inner surface of the variable shape-matching portion 211 is recessed concavely by the occlusal pressure to correspondingly shape-match with the convex outer surface of the implantation target portion 2. Accordingly, an intaglio groove corresponding to the implantation target portion 2 may be formed in the variable shape-matching portion 211 and corrected as a shape-matching correction portion 211r. Also, the outer surface of the pressing protrusion 212 may include a chewing trace formed by the occlusal pressure to correspond to a profile of an end of the matching target portion 3, for example, an end of a matching tooth t and may be corrected as an occlusal correction portion 212r. In addition, an interval between the shape-matching correction portion 211r and the occlusal correction portion 212r may be corrected to substantially correspond to the occlusal vertical dimension VD.

Also, each piece of the image data obtained while the general-purpose wax bite 210 with the shape-matching correction portion 211r and the occlusal correction portion 212r being formed and cured again is installed includes information of the occlusal vertical dimension VD.

As described above, since the general-purpose wax bite 210 is standardized to have a certain shape and mass-produced, manufacturing time and costs are economically reduced and the general-purpose wax bite 210 may be easily corrected to become a surface profile suitable for each person to be treated. Accordingly, precision/accuracy of the occlusal vertical dimension VD and each piece of the image data which is obtained by calculated/obtained using the corrected general-purpose wax bite 210 may be significantly improved.

The general-purpose wax bite 210 may be formed of paraffin wax that has a certain supporting strength of a solid at a room temperature and is softened when heated to a preset temperature or higher so as to be correctable to correspond to the implantation target portion 2 and the matching target portion 3. Also, since the paraffin wax is easily cut and corrected using a tool such as a knife or the like, when a natural/restored tooth remains in the implantation target portion 2 or a length of the general-purpose wax bite 210 is long, the paraffin wax may be used after being cut or divided. In addition, when the interdentium corresponding portion 212b (refer to FIG. 3A) or the alignment marker 214b (refer to FIG. 4) is formed on the pressing protrusion 212, the paraffin wax may be cut or divided on the basis thereof so that operational convenience in cutting and correction may be further improved.

Also, the paraffin wax has a melting point within a range of 47 to 64 r and may have a property of being softened even when high-temperature heat is not applied. Accordingly, the paraffin wax is safe even when being directly applied to the oral cavity when heated and is quickly cured at a temperature less than the preset temperature so that the degree of shape-matching between the implantation target portion 2 and the matching target portion 3 may be maintained. In addition, since the paraffin wax has a low contraction rate during a softening and curing process, the degree of shape-matching rate the implantation target portion 2 and the matching target portion 3 and precision of the calculated vertical dimension VD may be significantly improved.

Here, the paraffin wax includes paraffin (for example, ceresin) at 70 to 85 weight % and other additives at a residual weight % with respect to an entire weight %. For example, the paraffin wax may include ceresin at 77 to 85 weight %, beeswax at 7 to 13 weight %, carnauba wax at 1.5 to 3 weight %, resin at 2 to 4 weight %, and microcrystal wax at 1.5 to 3 weight %.

Meanwhile, the inner surface portion and the outer surface portion of the general-purpose wax bite 210 may be heated to a temperature within a range of 40 to 55° C. Also, the general-purpose wax bite 210 softened by heating each of the inner and outer surface portions is disposed between the implantation target portion 2 and the matching target portion 3 and occlusal pressure is applied to correspond to a preset vertical dimension VD. Here, the preset vertical dimension VD may be understood as an occlusal vertical dimension which allows the upper and lower jaws to occlude with each other while a person to be treated is in a suitable and comfortable state.

Accordingly, the inner surface portion of the general-purpose wax bite 210 is pressurized and corrected to correspond to the outer surface profile of the implantation target portion 2 and is integrally formed with the shape-matching correction portion 211r. Also, the outer surface portion of the general-purpose wax bite 210 is corrected by occlusion pressure to correspond to the matching target portion 3 and is integrally formed with the occlusal correction portion 212r. Here, the interval between the shape-matching correction portion 211r and the occlusal correction portion 212r may be formed to correspond to the occlusal vertical dimension VD.

Here, when the inner surface portion and the outer surface portions of the general-purpose wax bite 210 are heated to a temperature less than 40 r, the general-purpose wax bite 210 is not softened to have strength lower than the implantation target portion 2 and the matching target portion 3. Accordingly, even when occlusal pressure is applied, it is difficult to correct the inner and outer surface portions of the general-purpose wax bite 210 to correspond to the outer surface profiles of the implantation target portion 2 and the matching target portion 3. On the other hand, when the inner and outer surface portions of the general-purpose wax bite 210 are heated to a temperature higher than 55° C., the inner and outer surface portions excessively change to a liquid phase. Accordingly, fluidity of the inner and outer surface portions of the general-purpose wax bite 210 excessively increases so as not be corrected to have definite shapes corresponding to the implantation target portion 2 and the matching target portion 3. Also, when the general-purpose wax bite 210 is directly installed in the oral cavity, there is a risk such as a burn caused by a high temperature and the like.

Accordingly, the inner surface portion and the outer surface portion of the general-purpose wax bite 210 may be heated to a temperature within a range of 40 to 55 r to be softened to have strength lower than the implantation target portion 2 and the matching target portion 3 while maintaining a substantially corrected shape.

In addition, the general-purpose wax bite 210 may be heated only at the inner surface portion and the outer surface portion corresponding to the implantation target portion 2 and the matching target portion 3. Accordingly, an overall shape of the general-purpose wax bite 210 may be maintained while the inner surface portion and the outer surface portion may be easily corrected to be shape-matched/occluded with the implantation target portion 2 and the matching target portion 3.

Here, the general-purpose wax bite 210 may be placed into a container which accommodates warm water at a temperature of 45 to 55 r to be heated. Also, the general-purpose wax bite 210 may be heated using a heating device which discharges hot air, and any means configured to heat and soften the inner and outer surface portions of the general-purpose wax bite 210 may be applied to the present invention.

Here, to allow the shape-matching correction portion 211r to be attached to and closely shape-matched with the implantation target portion 2, the shape-matching correction portion 211r and the implantation target portion 2 may occlude with each other while being filled with an additional dental resin r1 therebetween and may be relined. That is, a gap or pore that may occur between the shape-matching correction portion 211r and the implantation target portion 2 as the paraffin wax is cured is filled with the dental resin and cured so that a shape matching rate between the shape-matching correction portion 211r and the implantation target portion 2 may be further improved.

Here, the dental resin may include a material having strength lower than tissue of a side of the implantation target portion 2 and minimally deformed by an external force after being cured. For example, the dental resin may include alginate, putty, a curable resin, or the like which are generally used when an impression is taken in a dental clinic and may have a coefficient of viscosity not allowing soft tissue of a gingival portion g of the implantation target portion 2 to be excessively pressurized and deformed.

Also, a maxillomandibular registration material such as a dental resin r2 is applied with a certain thickness to a side of the pressing protrusion 212 of the general-purpose wax bite 210 and coupled to the matching target portion 3 so that the occlusal vertical dimension VD and an installation position may be accurately set. Here, the dental resin r2 may include the same material as that of the dental resin r1 placed in the shape-matching correction portion 211r, and o in some cases, a wax rim may be laminated.

Accordingly, the shape-matching correction portion 211r is relined while a gap between the shape-matching correction portion 211r and the implantation target portion 2 is corrected. Also, an end side of the matching target portion 3 is corrected to be shape-matched and held by the outer surface portion side of the general-purpose wax bite 210. Accordingly, the general-purpose wax bite 210 may precisely guide the implantation target portion 2 and the matching target portion 3 to correspond to the occlusal vertical dimension VD.

In addition, since the shape-matching correction portion 211r is relined and is corrected to have an inner surface profile highly matched with the outer surface profile of the implantation target portion 2, precision of the dental restoration designed on the basis thereof may be significantly improved.

Meanwhile, the general-purpose wax bite 210 may have the inner surface portion corresponding to the implantation target portion 2 and the outer surface portion corresponding to the matching target portion 3 which are integrally formed to have a substantially single body. Accordingly, a different-type of wax and curable resin are laminated on the inner and outer surface portions of an occlusion-checking means such as a tray or a splint so that it is possible to basically remedy a conventional problem that a lamination part slides and is distorted laterally or a position is deformed. That is, since the occlusal pressure is substantially applicable in a vertical direction of the general-purpose wax bite 210, the precision of the calculated vertical dimension VD may be significantly improved.

On the basis of the general-purpose wax bite 210 corrected as described above, the implantation target portion 2 and the matching target portion 3 may be occlusion-arranged to correspond to the occlusal vertical dimension VD optimized for a person to be treated.

Here, when the general-purpose wax bite 210 is directly installed in the oral cavity and corrected, the occlusal vertical dimension VD may be determined by the expression of an opinion regarding the direct chewing sensitivity of the person to be treated. Meanwhile, the occlusal vertical dimension VD may be determined by measuring electrical/chemical signals of a temporomandibular joint periphery and jaw muscles. That is, as the person to be treated actually occludes upper and lower jaws with each other while the general-purpose wax bite 210 is inserted into the oral cavity, the general-purpose wax bite 210 may be corrected to correspond to the occlusal vertical dimension VD.

Alternatively, when the implantation target portion 2 and the matching target portion 3 are provided as impression models, the general-purpose wax bite 210 may be disposed between the impression models connected to the upper and lower jaw sides through an articulator. Also, as the impression models are occlusion-arranged to correspond to the occlusal vertical dimension VD statistically calculated in advance using the articulator, occlusal pressure may be applied. Accordingly, the inner surface portion and the outer surface portion of the general-purpose wax bite 210 may be corrected to be the shape-matching correction portion 211r and the occlusal correction portion 212r.

As described above, in the present invention, while costs are reduced using the general-purpose wax bite 210 provided as a ready-made article, an interval between surface profiles of the inner surface portion and the outer surface portion thereof may be separately corrected according to the occlusal vertical dimension VD of each person to be treated. Accordingly, the occlusal vertical dimension VD optimized for each person to be treated may be precisely calculated so that overall accuracy and precision of tooth restoration may be significantly improved.

Here, the general-purpose wax bite 210 may be disposed between the implantation target portion 2 and the matching target portion 3 and corrected according to the occlusal pressure before obtaining each piece of the image data.

Alternatively, image data regarding the implantation target portion 2 and the matching target portion 3 before installing the general-purpose wax bite 210 may be obtained in advance, and image data regarding the implantation target portion 2 and the matching target portion 3 after installing the general-purpose wax bite 210 may be obtained additionally.

Here, a method of processing the image data for designing a dental restoration may be performed through an image data processing system including the planning portion 230 (refer to FIG. 2).

Here, the planning portion 230 (refer to FIG. 2) includes a storage portion configured to store each piece of the image data and a processing portion configured to process the integrated scanned image and the three-dimensional planning image on the basis of each piece of image data to generate design information of the dental restoration. Also, an input portion configured to input information and a control command to the processing portion and an output portion configured to output the input information and control command, each piece of the image data, and the three-dimensional planning image or data generated by the processing portion such as the design information of the dental restoration are included.

In addition, the planning portion 230 (refer to FIG. 2) may further include a communication portion configured to receive each piece of the image data or transmit each piece of image data or the generated data to an external device. That is, each piece of the image data obtained using the image capturing device 220 (refer to FIG. 2) is transmitted to the planning portion 230 (refer to FIG. 3) through the communication portion, and each piece of image data or the generated data is transmitted to the manufacturing device 240 (refer to FIG. 2) through the communication portion.

Meanwhile, a plurality of scanned images of the implantation target portion and the matching target portion are obtained using an intraoral scanner. Also, a CT image of the oral cavity occluded through the general-purpose wax bite is obtained using the CT apparatus. Here, the plurality of scanned images may include scanned images obtained with respect to the implantation target portion and the matching target portion before the general-purpose wax bite is installed. In addition, a plurality of scanned images obtained with respect to the implantation target portion and the matching target portion after the corrected general-purpose wax bite is installed may be included (S220 in FIG. 1).

In detail, referring to FIG. 6, the plurality of scanned images may include a first scanned image m11 of an overall outer surface of the general-purpose wax bite corrected so that the shape-matching correction portion and the occlusal correction portion are integrally formed. Also, the plurality of scanned images may include a second scanned image m12 of an outer surface of the matching target portion and a third scanned image m13 of outer surfaces of the implantation target portion and the matching target portion which are occluded with each other through the corrected general-purpose wax bite.

Here, in the first scanned image m11, three-dimensional surface information v11 of the general-purpose wax bite which includes three-dimensional surface information m211r of the shape-matching correction portion and three-dimensional surface information m212r of the occlusal correction portion are shown as an image. Accordingly, in the first scanned image m11, the three-dimensional surface information m211r of the shape-matching correction portion is concavely shown and the three-dimensional surface information m212r of the occlusal correction portion continuously extending therefrom is shown to be convex toward the matching target portion side.

Also, in the second scanned image m12, three-dimensional surface information on the outer surface of the matching target portion is shown as an image. Here, when a matching tooth remains on the matching target portion, three-dimensional surface information t12 on the matching tooth is shown as an image in the second scanned image m12. Alternatively, when the matching target portion side is an edentulous jaw, three-dimensional surface information of the gingival portion of the matching target portion side may be shown as an image in the second scanned image m12. Also, in the operation of generating the three-dimensional planning image, standardized dental data of the matching target portion side prestored in the planning portion may be imaged and virtually arranged.

Also, in the third scanned image m13, three-dimensional surface information on an outer surface in an occlusion state in which the gingival portion of the implantation target portion is hidden by the inner surface portion side of the general-purpose wax bite and the end of the matching target portion is partially hidden by the outer surface portion side is shown as an image. Here, the third scanned image m13 is obtained while the implantation target portion and the matching target portion are occluded with each other through the general-purpose wax bite. Accordingly, in the third scanned image m13, three-dimensional surface information v13 of the general-purpose wax bite and three-dimensional surface information t13 of the matching tooth may be shown as an image.

Here, the third scanned image m13 is obtained by scanning the outer surfaces of the implantation target portion and the matching target portion to which the general-purpose wax bite is coupled. That is, the third scanned image m13 is obtained by scanning the oral cavity while biting the general-purpose wax bite or outer surfaces of the impression models are occlusion-arranged by the general-purpose wax bite. Accordingly, in the third scanned image m13, three-dimensional surface information corresponding to a labial-side outer surface and a partial buccal-side outer surface of the matching target portion and the general-purpose wax bite is shown as an image.

Hereinafter, it may be understood that the three-dimensional surface information means three-dimensional image information on a surface obtained through scanning and three-dimensional data means three-dimensional image information on internal tissue such as a shape/density and the like of the alveolar bone obtained through CT scanning That is, the three-dimensional surface information may be displayed as a three-dimensional image having a hollow therein and the three-dimensional data may be displayed as a three-dimensional image having a filled inside.

Here, the plurality of scanned images may be obtained by directly scanning the oral cavity of the person to be treated, using the intraoral scanner, before and after installing the general-purpose wax bite. In this case, a traction device configured to pull soft tissue such as the lips and buccal mucosa to be spaced apart from an outside of the gingival portion may be used.

However, the plurality of scanned images may be obtained by scanning, using the intraoral scanner, surfaces of the impression models corresponding to the implantation target portion and the matching target portion or the oral cavity. For example, when the person to be treated visits the practitioner side equipped with the intraoral scanner, the practitioner obtains the plurality of scanned images by capturing an image of the oral cavity of the person to be treated using the image capturing device. Alternatively, when the practitioner side is not equipped with the intraoral scanner, an impression model may be manufactured and then transferred to the manufacturer side and the plurality of scanned images may be obtained by capturing images of the impression model using a scanner provided at the manufacturer side.

Here, in the plurality of scanned images, a three-dimensional surface model having a substantial hollow is stored as a pixel unit or vector data. Here, when the implantation target portion and the matching target portion are provided as impression models, in order to minimize distortion of the scanned image, a fixed three-dimensional scanner may be used rather than a mobile scanner configured to scan while moving around an outside of a scanning target surface. Accordingly, dental curvature distortion of the implantation target portion and the matching target portion which are included in the scanned image may be minimized.

Meanwhile, the CT image m16 (refer to FIG. 8) may be obtained by directly capturing, using the CT apparatus, an image of the oral cavity while the general-purpose wax bite is coupled and occluded to correspond to the occlusal vertical dimension. Accordingly, in the CT image m16 (refer to FIG. 8), three-dimensional data and the like of the matching tooth of the matching target portion side and three-dimensional data a16 (refer to FIG. 8) of the alveolar bone of the implantation target portion side and three-dimensional data excluding soft tissue such as the lips, buccal mucosa, gingivae, and the like are imaged and displayed.

In addition, the general-purpose wax bite has a preset color to be clearly displayed in the plurality of scanned images while being formed to have a density less than 2.0 $g/cm^3$ to not be displayed in the CT image m16 (refer to FIG. 8). Accordingly, the CT image m16 (refer to FIG. 8) obtained while the general-purpose wax bite is installed and occluded is considered to have the occlusal vertical dimension while the alveolar bone of the implantation target portion side and the matching tooth/alveolar bone and the like of the matching target portion side are clearly displayed. Accordingly, accuracy and precision of each piece of image data obtained using the image capturing device may be significantly improved.

The plurality of scanned images obtained as described above and the CT image m16 (refer to FIG. 8) are transmitted to the planning portion. Also, through the following image alignment and matching process, the plurality of scanned images and the CT image m16 may be collected as information for establishing a tooth restoration plan using the dental restoration.

Meanwhile, the plurality of scanned images are aligned and arranged to correspond to the occlusal vertical dimension through the planning portion so that the integrated scanned image is generated. Also, the integrated scanned image is overlapped and matched with the CT image on the basis of a common part so that the three-dimensional planning image is generated (S230 in FIG. 1). Also, the dental restoration having a height in consideration of the occlusal vertical dimension is designed on the basis of the three-dimensional planning image and manufactured using the manufacturing device (S240 of FIG. 1).

Here, referring to FIGS. 7 to 9, the integrated scanned image m17 may be generated through the following operations.

In detail, the first scanned image m11 and the second scanned image m12 are overlapped and aligned on the basis of a common part with the third scanned image m13.

Here, referring to FIG. 7, concordance rates between image units of preset comparative areas of the first scanned image m11 and the second scanned image m12 and those of a corresponding area of the third scanned image m13 are calculated and compared. Here, when the concordance rates are higher than or equal to a preset setting value, the comparative areas of the first scanned image m11 and the second scanned image m12 are aligned and arranged in the corresponding area of the third scanned image m13 to be swapped. Here, swapping may be preferably understood as a preset image that is substituted or exchanged with another image or a modified image according to image processing.

The comparative areas and the corresponding area may be set to be common parts commonly included in the scanned images and may be set to be particular parts having a boundary clearly distinguished from a periphery while having hard tissue to minimize fluidity. That is, an interdentium, a stepped portion of the general-purpose wax bite, or the boundary between the respective images may be set to be the above-described particular part.

For example, in the first scanned image m11 and the third scanned image m13, particular parts of the three-dimensional surface information v11 and v13 of the general-purpose wax bite displayed equally in the respective images may be selected as common parts and set to be overlapping reference points. Also, in the second scanned image m12 and the third scanned image m13, particular parts of the three-dimensional surface information t12 and t13 of the matching tooth displayed equally in the respective images may be selected as common parts and set to be overlapping reference points. The overlapping reference points may be set to be a plurality of places.

In detail, the comparative areas and the corresponding area selected from the respective pieces of three-dimensional surface information are compared in preset image units. For example, the concordance rates between the comparative areas of the respective pieces of three-dimensional surface information and the corresponding area corresponding thereto may be calculated and compared by a pixel unit or vector data. Also, when the concordance rates are higher than or equal to the preset setting value, a degree of shape-matching of a state in which the respective pieces of three-dimensional surface information including the comparative areas and the corresponding area are overlapped may be significantly improved. Accordingly, the first scanned image m11 and the second scanned image m12 are aligned and arranged in consideration of the occlusal vertical dimension VD on the basis of the third scanned image m13.

Meanwhile, referring to FIG. 9, the first scanned image m11 may be swapped to externally expose the three-dimensional surface information m211r of the shape-matching correction portion concavely recessed inward, which corresponds to the inner surface portion of the general-purpose wax bite. Here, the three-dimensional surface information m211r of the shape-matching portion may be understood as three-dimensional surface information obtained by scanning the general-purpose wax bite corrected to allow the shape-matching correction portion to be shape-matched with the outer surface profile of the implantation target portion through a series of operations to be described below.

Accordingly, the three-dimensional surface information m211r of the shape-matching correction portion and the three-dimensional surface information on the outer surface of the matching target portion are aligned and arranged in a state in which the occlusal vertical dimension VD is considered to be generated as the integrated scanned image m17.

In detail, the first scanned image m11 may include three-dimensional surface information on an overall outer surface of the general-purpose wax bite in which the inner and outer surface portions are corrected by the occlusal pressure. Hereinafter, the three-dimensional surface information of the general-purpose wax bite may be understood as three-dimensional surface information of the general-purpose wax bite in the state in which the inner and outer surface portions are corrected.

The three-dimensional surface information of the general-purpose wax bite is stored while a plurality of points having preset coordinate values are mutually connected. For example, the three-dimensional surface information of the general-purpose wax bite may be stored as a StereoLithography (STL) file and forms a triangular surface by the plurality of points and lines connecting the same corresponding to an outer surface shape of the general-purpose wax bite. Accordingly, the three-dimensional surface information of the general-purpose wax bite may be stored as a three-dimensional surface model having a substantially hollow interior.

Here, the three-dimensional surface information of the general-purpose wax bite includes the three-dimensional surface information m212r of the occlusal correction portion on the outer surface portion side displayed to be convex outward. Also, the three-dimensional surface information of the general-purpose wax bite includes the three-dimensional surface information m211r of the shape-matching correction portion on the inner surface portion side displayed to be concave inward.

Here, a boundary line x is set between the three-dimensional surface information on the outer surface portion and the three-dimensional surface information m211r of the shape-matching correction portion of the general-purpose wax bite. Here, the boundary line x may be set along an area spaced at a certain interval apart from an outside of an outer edge of the shape-matching correction portion 211. Here, the outer edge of the three-dimensional surface information m211r of the shape-matching correction portion may be understood as a line set corresponding to an outermost edge of the margin 211a (refer to FIG. 3A).

Also, three-dimensional surface information of the pressing protrusion side is set to be a deletion area d. Also, an image is swapped so that the deletion area d is deleted and the three-dimensional surface information m211r of the shape-matching correction portion is exposed to be convex toward the matching target portion side. Here, in the present invention, "being deleted" may be understood as including deleting and making an image or data selected from overall image data transparent and invisible.

Meanwhile, the three-dimensional surface information of the general-purpose wax bite is stored as surface information without a substantial thickness. Accordingly, the three-dimensional surface information m211r of the shape-matching correction portion has coordinate values for an inner surface side profile and coordinate values for an outer surface side profile which are substantially equal. Also, the three-dimensional surface information m211r of the shape-matching correction portion is obtained while being corrected to substantially shape-match and correspond to an outer surface profile of the implantation target portion. Accordingly, the three-dimensional surface information m211r of the shape-matching correction portion substantially corresponds to the outer surface profile of the gingival portion of the implantation target portion. Here, part m21 shown in FIGS. 7B to 9 may be understood as meaning the first scanned image swapped while the three-dimensional surface information m211r of the shape-matching correction portion is exposed outward.

Through the image processing process, the first scanned image m11 including the three-dimensional surface information of the general-purpose wax bite is swapped so that the three-dimensional surface information on the outer surface profile of the gingival portion of the implantation target portion may be easily obtained. In addition, instead of the oral cavity with fluidity of the gingiva that is soft tissue, three-dimensional surface information corresponding to the implantation target portion is obtained from the scanned image of the general-purpose wax bite having firm strength in a hardened state even though having fluidity correctable by the occlusal pressure in a softened state. Accordingly, reliability of image information for designing the dental restoration may be significantly improved.

Also, the swapped first scanned image m21 and the second scanned image m12 are aligned and arranged so that the integrated scanned image m17 is obtained. The integrated scanned image m17 is displayed while the three-dimensional surface information m211r of the shape-matching correction portion of the general-purpose wax bite exposed toward the matching target portion side and the three-dimensional surface information t12 of the matching tooth are spaced apart corresponding to the occlusal vertical dimension VD.

Here, to clearly display the second scanned image m12 and the swapped first scanned image m21, the third scanned image m13 may be deleted from the integrated scanned image m17.

Meanwhile, referring to FIG. 8, a part commonly displayed in the integrated scanned image m17 and the CT image m16 is set to be a matching reference point so that the integrated scanned image m17 and the CT image m16 are overlapped and matched. Accordingly, there is generated a three-dimensional planning image m20 including the three-dimensional surface information m211r of the shape-matching correction portion displayed in the swapped first scanned image m21, the three-dimensional data a16 of the alveolar bone on the implantation target portion side, and the three-dimensional surface information t12 and three-dimensional data of the matching tooth. Here, the three-dimensional data of the matching tooth displayed in the CT image m16 may be matched with the three-dimensional surface information t12 of the matching tooth displayed in the integrated scanned image m17 to be integrally and substantially overlapped therewith.

Here, the integrated scanned image m17 is obtained by aligning and arranging the first scanned image m11 and the second scanned image m12 on the basis of the third scanned image m13. Also, the CT image m16 is obtained by taking an image of the oral cavity while the general-purpose wax bite is coupled. Accordingly, the three-dimensional surface information and three-dimensional data which are displayed in the CT image m16 and the integrated scanned image m17 are aligned and matched with each other corresponding to substantially the same vertical dimension VD. Accordingly, initial planning data in which an error in matching the integrated scanned image m17 with the CT image m16 is minimized may be obtained. Accordingly, the respective pieces of image data may be easily matched and a matching process may be simplified while accuracy and precision of collected information may be significantly improved.

A height of the dental restoration is set on the basis of the three-dimensional planning image m20 generated as described above. Also, design information c20 of the dental restoration having a masticating surface shape set in consideration of the three-dimensional surface information t12 of the matching tooth or standard dental data is virtually disposed in the three-dimensional planning image m20.

Also, an implantation position and a direction h20 of a fixture are set through the three-dimensional data a16 of the alveolar bone on the implantation target portion side based on the CT image m16. Also, a virtual fixture f20 supporting a masticating pressure is virtually disposed corresponding to the implantation position and the direction h20 while a real fixture corresponding to the virtual fixture f20 is prepared or manufactured. In addition, a real abutment mediating between the real fixture and a real dental restoration manufactured on the basis of the design information c20 of the dental restoration is prepared or manufactured.

Subsequently, the design information c20 of the dental restoration is transmitted from the planning portion to the manufacturing device and the real dental restoration is manufactured. Here, the three-dimensional planning image m20 may be stored as a standard file of a three-dimensional printer, such as the above-described STL file. Accordingly, a real dental restoration precisely corresponding to the design information c20 of the dental restoration may be easily manufactured. Of course, the real dental restoration may be manufactured using a milling device or a molding device.

Meanwhile, the surgical guide may be designed on the basis of the three-dimensional planning image m20. Also, a real surgical guide based on design information of the surgical guide may be manufactured with the real dental restoration using the manufacturing device.

That is, in the present invention, the dental restoration and the surgical guide may be designed and manufactured at the same time on the basis of the three-dimensional planning image m20. Accordingly, the number of visits to the dental clinic by the person to be treated may be minimized, and basic technology and device configured to complete implantation of the fixture/abutment and installation of the dental restoration in a short time may be provided.

Figure 10:
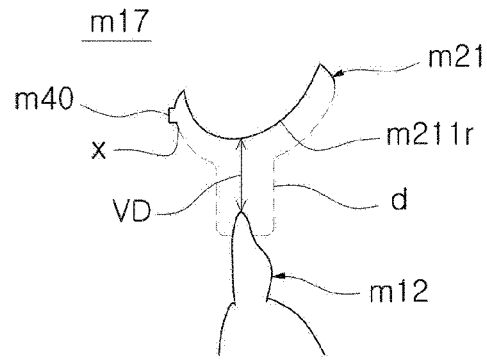
FIG. 10 is an exemplary view illustrating a modified example of the integrated scanned image of the image data processing method in the method of manufacturing a dental restoration according to one embodiment of the present invention.

Meanwhile, FIG. 10 is an exemplary view illustrating a modified example of the integrated scanned image in the image data processing method for designing the dental restoration according to one embodiment of the present invention. Since basic components of the modified example except a matching marker are the same as those of the above-described embodiment, a detailed description of the same components will be omitted.

As shown in FIG. 10, an operation of attaching a plurality of matching markers to the outer surface of the general-purpose wax bite may be further included in the operation of obtaining each piece of image data. The matching markers may be attached to the outer surface side of the implantation target portion exposed outward from the general-purpose wax bite. Particularly, the matching markers may be attached when the implantation target portion is a substantially edentulous jaw without residual/restored teeth or when residual restored teeth are metallic materials.

Here, three or more matching markers may be provided/formed while being spaced apart along the outer surface of the gingival portion of the implantation target portion side. The matching markers may be provided as a solid body having a preset volume and attached to the implantation target portion. A dental resin having a density through which radiation does not pass may be injected with a certain size onto the outer surface of the implantation target portion and cured to be attached.

Accordingly, in each piece of image data including an image with respect to the general-purpose wax bite, the matching markers may be displayed as an image.

That is, in the CT image, the matching markers may be imagified and displayed outside alveolar bone data of the implantation target portion. Also, when the integrated scanned image and the CT image are matched by the planning portion, three-dimensional surface information/data of the matching markers displayed in each piece of image data may be set to be a common part. Accordingly, a degree of shape-matching between the integrated scanned image and the CT image may be significantly improved.

Here, each piece of the image data including the image of the general-purpose wax bite may be understood to be the first scanned image, the third scanned image, and the CT image m16.

In detail, in the first scanned image and the third scanned image, three-dimensional surface information m40 of the matching markers is displayed. Also, in the CT image m16, three-dimensional data of the matching markers is displayed. Here, to not substantially display image information on the general-purpose wax bite in the CT image, the matching markers may be provided/formed as a radiation-impermeable material while the general-purpose wax bite is provided as a radiation-permeable material.

Accordingly, in each piece of the image data including the three-dimensional data and the three-dimensional surface information of the general-purpose wax bite, the three-dimensional surface information m40 and the three-dimensional data of the matching markers may be displayed at substantially the same positions. Also, the three-dimensional data and the three-dimensional surface information m40 of the matching markers are overlapped as common parts so that the integrated scanned image m17 and the CT image m16 may be precisely matched corresponding to the occlusal vertical dimension VD.

Here, in the operation of swapping the first scanned image, the boundary line x may be set so that the three-dimensional surface information m40 of the matching markers is connected to and included in the three-dimensional surface information m211r of the shape-matching correction portion of the general-purpose wax bite. That is, the deletion area d may be set as the remaining part excluding the three-dimensional surface information m211r of the shape-matching correction portion and the three-dimensional surface information m40 of the matching markers.

Accordingly, the integrated scanned image m17 is generated by aligning and arranging intervals between the three-dimensional surface information m211r of the shape-matching correction portion including the three-dimensional surface information m40 of the matching markers and the three-dimensional surface information of the matching target portion included in the second scanned image m12 corresponding to the occlusal vertical dimension VD. Also, the integrated scanned image m17 and the CT image m16 are matched and processed on the basis of the common parts such as the three-dimensional surface information m40 of the matching markers, the three-dimensional surface information t12 of the matching tooth, and the like.

Through the image processing process, insufficient information in each piece of the image data may be mutually compensated/corrected. That is, as shown in FIG. 8, the three-dimensional surface information on the gingival portion of the implantation target portion which is not displayed in the CT image m16 may be compensated for from the integrated scanned image m17. Also, even when a distortion of dental curvature occurs in the plurality of scanned images in a scanning process using the intraoral scanner, correction may be performed on the basis of an accurate dental curvature of the CT image m16. Accordingly, the three-dimensional planning image m20 may be generated by high-precisely matching each piece of the image data including information for designing the dental restoration.

Of course, when a plurality of natural teeth or nonmetallic restored teeth remain on the implantation target portion, even when an additional matching marker is not attached, three-dimensional surface information and data of the residual teeth may be set to be a matching reference point.

In addition, in the integrated scanned image, the three-dimensional surface information t12 of the matching tooth included in the second scanned image m12 may be aligned and disposed to match the three-dimensional surface information m212r of the occlusal correction portion included in the first scanned image m11. To this end, in the first scanned image m1l, boundary lines are formed an outer edge of the three-dimensional surface information m211r of the shape-matching correction portion and an outer edge of the three-dimensional surface information m212r of the occlusal correction portion while a space between the boundary lines may be set to be a deletion area.

Also, the deletion area is deleted so that the three-dimensional surface information m211r of the shape-matching correction portion and the three-dimensional surface information m212r of the occlusal correction portion are swapped to be exposed outward. Here, a gap between the three-dimensional surface information m211r of the shape-matching correction portion and the three-dimensional surface information m212r of the occlusal correction portion is set to be an interval corresponding to the occlusal vertical dimension VD (refer to FIG. 10) by occlusal pressure. Accordingly, the three-dimensional surface information m212r of the occlusal correction portion and the three-dimensional surface information t12 of the matching tooth are overlapped and arranged while a mutually corresponding part thereof is set as an overlapping reference point so that the integrated scanned image may be easily obtained.

Figure 11:
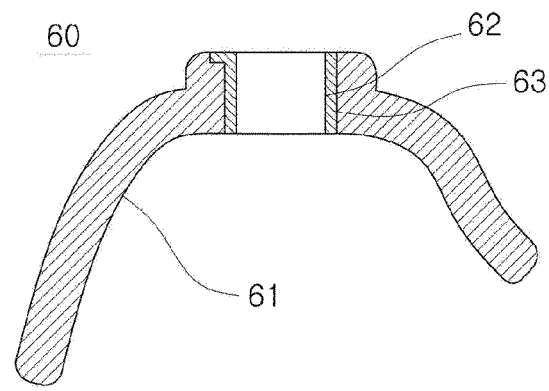
FIG. 11 is an exemplary cross-sectional view illustrating a surgical guide manufactured according to one embodiment of the present invention.

Meanwhile, FIG. 11 is an exemplary cross-sectional view illustrating a surgical guide 60 manufactured according to one embodiment of the present invention.

As shown in FIG. 11, the surgical guide 60 is set on the basis of the three-dimensional surface information of the shape-matching correction portion so that a fixing groove portion 61 is substantially shape-matched with the outer surface profile of the gingival portion of the implantation target portion of the oral cavity. Accordingly, an inner surface profile of the fixing groove portion 61 is designed and manufactured to be shape-matched with the implantation target portion so that the surgical guide 60 may be installed/fixed on and to a precise position of the oral cavity.

Also, a guide hole 62 is formed to have a diameter for substantially rotating a drill or an implantation tool while a separate sleeve 63 may be coupled thereto to minimize deformation caused by stress and frictional heat which occur in high-speed rotation.

The sleeve 63 may be coupled to not rotate along with high-speed rotation of the drill or the implantation tool and formed of a brass material to support the stress generated in high-speed rotation and to reduce the frictional heat. Also, an inner circumferential diameter of the sleeve 63 is substantially formed to be an inner circumferential diameter of the guide hole 62. Accordingly, even when a drilling operation is repetitively performed while an implantation hole is formed and the fixture is implanted, an accurate implantation position of the fixture may be continuously guided.

Meanwhile, referring to FIGS. 1 to 11, the general-purpose wax bite 210 or 210A and the image capturing device 220 may be provided on the practitioner side. When the person to be treated visits the practitioner side, the plurality of scanned images and the CT image m16 may be obtained using the image capturing device 220 and stored in a terminal of the practitioner side. Here, the general-purpose wax bite 210 or 210A is prepared with a ready-made article and corrected to correspond to each person to be treated. Also, the plurality of scanned images and the CT image m16 are obtained on the basis of the corrected general-purpose wax bite 210 or 210A in consideration of the occlusal vertical dimension VD.

Also, the plurality of scanned images and the CT image m16 which are stored in the terminal of the practitioner side are transmitted to a server of the manufacturer side.

Meanwhile, the server of the manufacturer side may include the planning portion 230, and the integrated scanned image m17 and the three-dimensional planning image m20 are generated and stored through the planning portion 230. Also, the dental restoration and the surgical guide 60 are designed on the basis of the three-dimensional planning image m20. Of course, in some cases, the terminal of the practitioner may also include the planning portion 230. Here, the integrated scanned image m17 may be generated by the planning portion 230 included in the terminal of the practitioner side and transmitted, with the CT image m16, to the server of the manufacturer side.

Subsequently, design information of the dental restoration and the design information of the surgical guide 60 are transmitted to the manufacturing device 240 so that the real dental restoration and the real surgical guide 60 are manufactured. Here, in order to deliver the manufactured real dental restoration and real surgical guide 60 to the practitioner side, delivery information including a requested address of the terminal of the practitioner side is output.

Also, when the real dental restoration and the real surgical guide 60 are delivered to the practitioner side, the real surgical guide 60 is installed/fixed in and to the oral cavity of the person to be treated who visits the practitioner side again. Subsequently, a real fixture/abutment corresponding to the real dental restoration may be implanted and the real dental restoration may be continuously installed after removing the surgical guide 60.

As described above, in the present invention, the number of visits, by the person to be treated, to the dental clinic and the number of times of transmitting each piece of the image data for designing the dental restoration and the surgical guide 60 are minimized. Accordingly, inconvenience of the person to be treated may be minimized and an overall period of time consumed for restoring using the dental restoration may be significantly reduced. Also, since a failure rate caused by an error in pieces of collected information due to an increase in numbers of transmitting/delivering an image/product and a problem caused by misdelivering a product are basically remedied, precision of installing the dental restoration may be significantly improved.

Accordingly, in the present invention, an occlusal vertical dimension may be calculated using a simple method of applying occlusal pressure while the inner and outer surface portions of the general-purpose wax bite 210 or 210A prepared as standardized ready-made articles of various sizes are heated. Accordingly, unlike using a splint which is customized and increases cost/time or a tracer which is inconvenient to operate, time and costs consumed for calculating the occlusal vertical dimension may be reduced while convenience in use may be significantly improved.

Here, the general-purpose wax bite 210 or 210A may be formed of paraffin wax to be easily deformed corresponding to the gingival portion g that is soft tissue when occluded a temperature higher than or equal to a preset temperature as well as being easily cured so as to precisely guide an occlusal vertical dimension. Also, since it is possible to correct the general-purpose wax bite 210 or 210A and obtain each piece of image data at one time when a person to be treated visits a dental clinic once, an overall period and cost of tooth restoration may be significantly reduced.

In addition, since occlusal pressure is uniformly transferred corresponding to an occlusal direction as the general-purpose wax bite 210 or 210A is manufactured as one body using paraffin wax, distortion or damage may be minimized. Accordingly, the shape-matching correction portion 211*r* and the occlusal correction portion 212*r* may be accurately and precisely obtained on the inner and outer surface portions of the general-purpose wax bite 210 or 210A so as to significantly improve reliability of information collected on the basis thereof.

In addition, the shape-matching correction portion 211*r* is relined by curable resin and corrected to have a high shape-matching rate with the implantation target portion. Accordingly, instead of the implantation target portion 2 most of which is highly fluid gingival tissue, accuracy information may be obtained through scanned images of the shape-matching correction portion 211*r*. Accordingly, precision in designing and manufacturing the dental restoration may be significantly improved.

Also, in the present invention, clear design information may be obtained from the three-dimensional surface information of the general-purpose wax bite in which an inner surface profile is shape-matched with an outer surface profile of the implantation target portion. Accordingly, the outer surface profile may replace the implantation target portion that is an edentulous jaw having highly fluid gingiva causing difficulty in obtaining precise three-dimensional surface information. Accordingly, precision of initially generated planning data may be significantly improved and accuracy in installing the dental restoration manufactured on the basis thereof may be significantly improved.

Also, an unnecessary image part is deleted from three-dimensional surface information obtained by scanning the general-purpose wax bite and is swapped so as to expose the three-dimensional surface information of the shape-matching correction portion shape-matched with the outer surface profile of the implantation target portion. Since image information for designing the dental restoration is obtained using the above simple method, the image processing process for generating the three-dimensional planning image may be quick and simplified.

Figure 12:
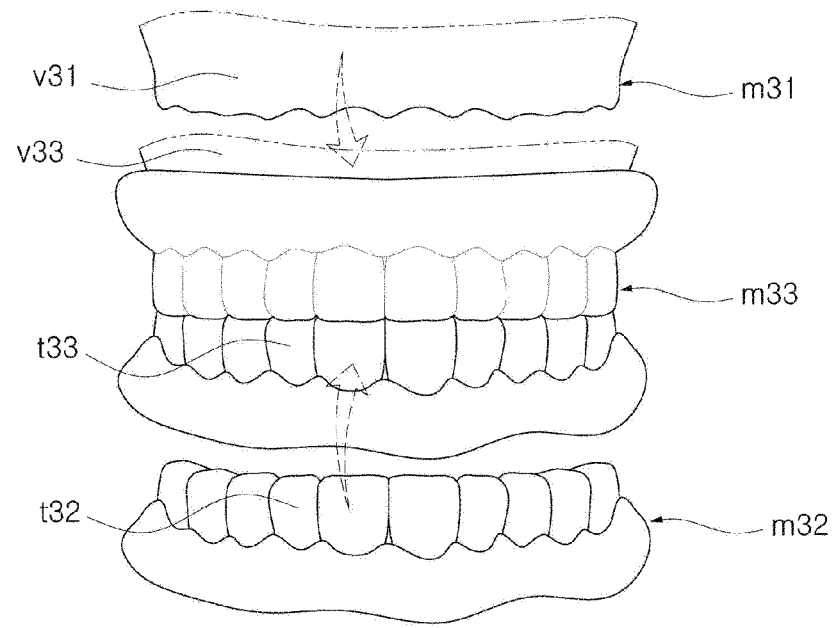
FIG. 12 is an exemplary view illustrating a process of aligning and arranging scanning images of an image data processing method in a method of manufacturing a dental restoration according to another embodiment of the present invention.
Figure 13:
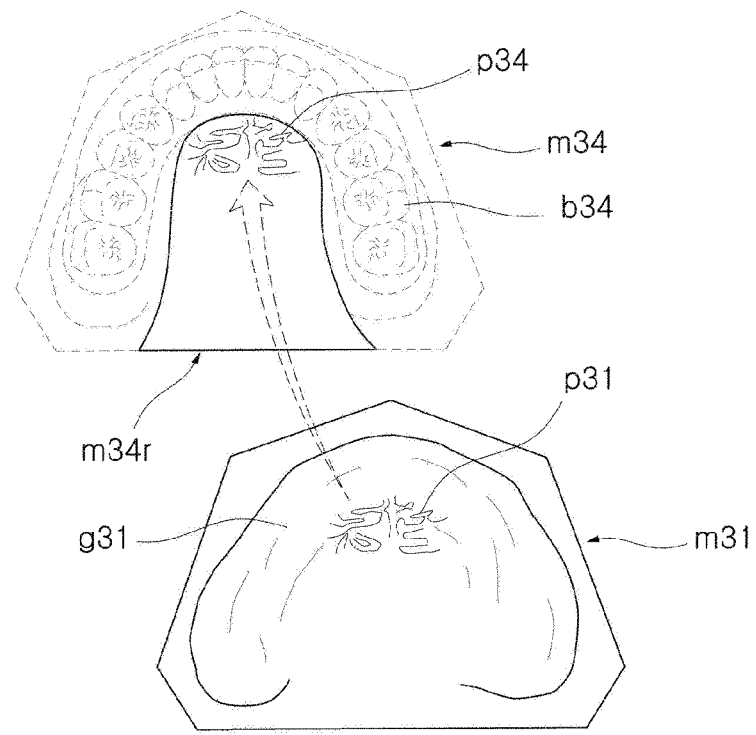
FIG. 13 is an exemplary view illustrating a state in which a first scanning image of the image data processing method is swapped in the method of manufacturing a dental restoration according to another embodiment of the present invention.

FIG. 12 is an exemplary view illustrating a process of aligning and arranging scanning images of an image data processing method in a method of manufacturing a dental restoration according to another embodiment of the present invention, and FIG. 13 is an exemplary view illustrating a state in which a first scanning image of the image data processing method is swapped in the method of manufacturing a dental restoration according to another embodiment of the present invention. Also, FIG. 14 is an exemplary view illustrating a three-dimensional planning image of the image data processing method in the method of manufacturing a dental restoration according to another embodiment of the present invention.

In the embodiment, as basic components and an image data processing method except obtaining a fourth scanned image m34 are the same as the above-described embodiment, a detailed description on the same components and processing method will be omitted. Also, it may be understood that an implantation position and direction h50 of a virtual fixture f50 shown in the respective drawings illustrating another embodiment of the present invention are substantially the same as an implantation position and direction h50 of the virtual fixture f20 shown in the respective drawings illustrating the above-described embodiment.

Figure 14:
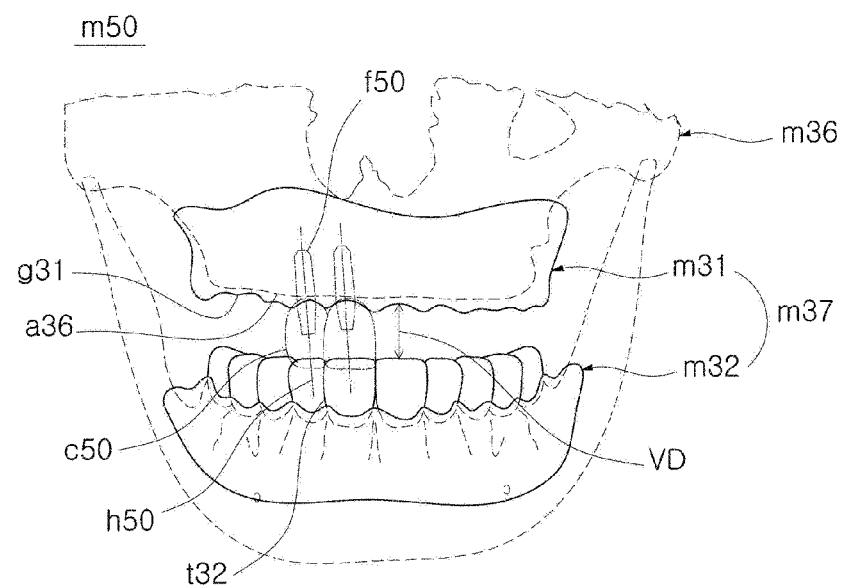
FIG. 14 is an exemplary view illustrating a three-dimensional planning image of the image data processing method in the method of manufacturing a dental restoration according to another embodiment of the present invention.

As shown in FIGS. 12 to 14, the first scanned image m31 includes three-dimensional surface information v31 of the implantation target portion side exposed to the gingival portion and hard palate as a whole. For example, three-dimensional surface information g31 of the gingival portion and three-dimensional surface information p31 of the hard palate continuously connected thereto are imaged and displayed in the first scanned image m31. Also, in the second scanned image m32, three-dimensional surface information on the outer surface of the matching target portion is shown as an image. Here, when a matching tooth remains on the matching target portion, three-dimensional surface information t32 of a matching tooth may be shown as an image in the second scanned image m32. Also, in the third scanned image m33, three-dimensional surface information v33 of the general-purpose wax bite and three-dimensional surface information t33 of the matching tooth may be shown as an image.

In detail, referring to FIG. 12, concordance rates between image units of preset comparative areas of the first scanned image m31 and the second scanned image m32 and those of a corresponding area of the third scanned image m33 are calculated and compared. Here, image unit may be understood as being obtained by dividing each piece of the three-dimensional surface information by a minimum unit or a preset unit and as including a pixel unit or a vector data unit.

Here, the comparative areas and the corresponding area calculated by selecting common parts from the respective pieces of three-dimensional surface information are compared in preset image units. Accordingly, the first scanned image m31 is overlapped with the implantation target portion side of the third scanned image m33 and the second scanned image m32 is overlapped with the matching target portion side of the third scanned image m33. Here, the first scanned image m31 and the second scanned image m32 are aligned and arranged corresponding to the occlusal vertical dimension.

Also, referring to FIG. 14, a part commonly displayed in the integrated scanned image m37 and the CT image m36 is set to be a matching reference point so that the integrated scanned image m37 and the CT image m36 are overlapped and matched. Accordingly, there is generated the three-dimensional planning image m50 including three-dimensional surface information g31 of the gingival portion of the implantation target portion side displayed in the first scanned image m31, three-dimensional data a36 of the alveolar bone on the implantation target portion side, and the three-dimensional surface information t32 and three-dimensional data of the matching tooth. Also, design information c50 of the dental restoration having a masticating surface shape set in consideration of the three-dimensional surface information t32 of the matching tooth or standard dental data is virtually disposed in the three-dimensional planning image m50.

Meanwhile, as shown in FIGS. 12 and 13, the fourth scanned image m34 of the outer surface of the implantation target portion to which the general-purpose wax bite is coupled may be obtained. In detail, the fourth scanned image m34 is obtained while the general-purpose wax bite is coupled to the implantation target portion so that the gingival portion is substantially hidden. Accordingly, the fourth scanned image m34 includes three-dimensional surface information b34 of the general-purpose wax bite and three-dimensional surface information on the outer surface of the implantation target portion side exposed outward from the general-purpose wax bite. For example, in the fourth scanned image m34, the three-dimensional surface information b34 of the general-purpose wax bite and three-dimensional surface information p34 of the hard palate are shown as an image.

Also, in the general-purpose wax bite, the shape-matching correction portion is shape-matched with and coupled to the gingival portion of the implantation target portion. Accordingly, a position of the three-dimensional surface information of the general-purpose wax bite included in the fourth scanned image m34 substantially corresponds to a position of the three-dimensional surface information b34 of the general-purpose wax bite included in the third scanned image m33.

Also, the fourth scanned image m34 is overlapped with the third scanned image m33 on the basis of the common part therebetween. Here, through an image processing process of swapping the fourth scanned image m34 with the first scanned image m31, the three-dimensional surface information g31 of the gingival portion of the implantation target portion side is aligned corresponding to the three-dimensional surface information of the matching tooth and the occlusal vertical dimension.

In detail, concordance rates between image units of a preset first comparative area of the fourth scanned image m34 and a first corresponding area of the third scanned image m33 are compared and calculated. Also, when the concordance rate is higher than or equal to a preset setting value, the first comparative area is aligned with the first corresponding area.

Here, the first comparative area and the first corresponding area may be understood as the three-dimensional surface information b34 of the general-purpose wax bite equally included in the respective scanned images. That is, the three-dimensional surface information b34 of the general-purpose wax bite included in the fourth scanned image m34 is set to be the first comparative area and the three-dimensional surface information of the general-purpose wax bite included in the third scanned image m33 is set to be the first corresponding area. Also, when a concordance rate between the first comparative area and the first corresponding area is higher than or equal to a preset setting value, they are calculated as a common part so that the respective scanned images may be highly shape-matched and overlapped.

Here, the first scanned image m31 may be overlapped with the fourth scanned image m34 aligned on the basis of the third scanned image m33 on the basis of common firm tissue therebetween. Accordingly, the fourth scanned image m34 may be swapped with the first scanned image m31.

In detail, concordance rates between image units of a preset second comparative area of the first scanned image m31 and a second corresponding area of the fourth scanned image m34 are compared and calculated. Also, when the concordance rate is higher than or equal to a preset setting value, the second comparative area is aligned with the second corresponding area.

Here, the second comparative area and the second corresponding area may be understood as the three-dimensional surface information of the hard palate equally included in the respective scanned images. For example, when the implantation target portion is an upper jaw, the three-dimensional surface information p31 of the hard palate included in the first scanned image m31 is set to be the second comparative area. Also, three-dimensional surface information p34 of the hard palate included in the fourth scanned image m34 is set to be the second corresponding area, and a concordance rate with the second comparative area is compared and calculated. Also, when the calculated concordance rate is higher than or equal to a preset setting value, they are calculated as a common part so that the respective scanned images may be highly shape-matched and overlapped.

In detail, in the third scanned image m33, the gingival portion of the implantation target portion side is hidden by the general-purpose wax bite and only partial three-dimensional surface information of a labial side is substantially included. Here, the fourth scanned image m34 including the three-dimensional surface information b34 of the general-purpose wax bite is overlapped first with the third scanned image m33. Meanwhile, in the fourth scanned image m34, the three-dimensional surface information b34 of the general-purpose wax bite and the three-dimensional surface information p34 of the hard palate are included. Also, the fourth scanned image m34 undergoes an image processing process of being swapped to be replaced with the first scanned image m21. Accordingly, the three-dimensional surface information g31 of the gingival portion of the implantation target portion side may be aligned to correspond to the three-dimensional surface information t32 of the matching tooth and the accurate vertical dimension.

As described above, the fourth scanned image m34 including all common parts corresponding to the first scanned image m31 and the third scanned image m34 is obtained and image-processed. Also, scanned images including three-dimensional surface information of firm tissue such as the three-dimensional surface information b34 of the general-purpose wax bite and the three-dimensional surface information p31 and p34 of the hard palate are coupled to each other. Accordingly, three-dimensional surface information of the implantation target portion side that is an edentulous jaw may be precisely aligned and arranged by coupling the scanned images.

Accordingly, since the concordance rate between the respective scanned images is significantly improved, accuracy and precision of image information may be significantly improved. Also, since the respective pieces of three-dimensional surface information may be automatically overlapped and aligned when the calculated concordance rate is higher than or equal to the preset setting value, working convenience in image processing may be significantly improved.

In addition, in the fourth scanned image m34, the three-dimensional surface information b34 of the general-purpose wax bite is set to be a deletion area and deleted to be regained as a fourth corrected scanned image m34r. Accordingly, the fourth corrected scanned image m34r includes the three-dimensional surface information p34 of the hard palate. Here, it may be understood that the three-dimensional surface information b34 of the general-purpose wax bite being displayed as a dotted line indicates being set to be the deletion area and a deleted state.

Also, image units of a preset third comparative area of the first scanned image m31 and a third corresponding area of the fourth scanned image m34r are compared and a concordance rate therebetween is calculated. Here, when the calculated concordance rate is higher than or equal to a preset setting value, the third comparative area is aligned with the third corresponding area so that the fourth corrected scanned image m34r is swapped with the first scanned image m31. Here, the third comparative area and the third corresponding area may be understood as the three-dimensional surface information p31 and p34 of the hard palate included in the respective scanned images.

Here, as the three-dimensional surface information b34 of the general-purpose wax bite is deleted from the fourth scanned image m34, the time consumed for comparing and calculating the first scanned image m31 may be significantly reduced. Also, since the fourth scanned image m34 and the first scanned image m31 are compared and substantially unnecessary information is deleted, concordance rates among the respective scanned images may be significantly improved.

Figure 15:
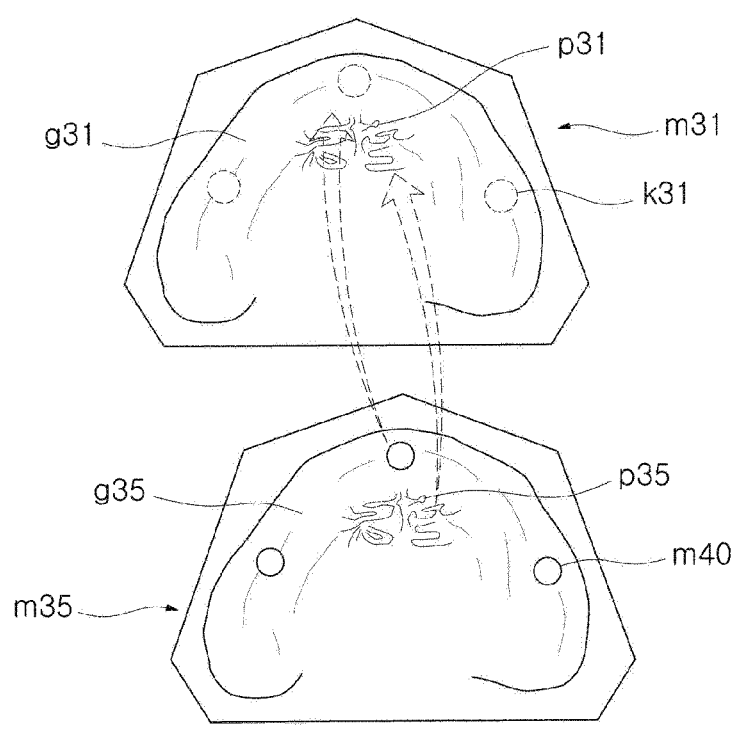
FIG. 15 is an exemplary view illustrating a modified example of an integrated scanned image of the image data processing method in the method of manufacturing a dental restoration according to another embodiment of the present invention.

Meanwhile, FIG. 15 is an exemplary view illustrating a modified example of an integrated scanned image of the image data processing method in the method of manufacturing a dental restoration according to another embodiment of the present invention. Since basic components of the modified example except a fifth scanned image and a matching marker are the same as those of the above-described one embodiment, a detailed description of the same components will be omitted.

As shown in FIG. 15, a fifth scanned image m35 of an overall outer surface of the implantation target portion to which the matching marker is attached may be further obtained. That is, in the fifth scanned image m35, three-dimensional surface information g35 of the gingival portion of the implantation target portion side, three-dimensional surface information p35 of the hard palate, and the three-dimensional surface information m40 of the matching marker may be included. In addition, at least the fifth scanned image m35 and the CT image m36 may be obtained after the matching marker is attached to the implantation target portion side.

Here, the first scanned image m31 is swapped to be aligned and disposed on the implantation target portion side of the third scanned image through the above-described image processing process. Here, the fifth scanned image m35 may be overlapped and swapped on the basis of a common part with the first scanned image m31.

In detail, image units of a preset fourth comparative area of the fifth scanned image m35 and a fourth corresponding area of the first scanned image are compared and a concordance rate therebetween is calculated. Here, when the calculated concordance rate is higher than or equal to a preset setting value, the fourth comparative area is aligned with the fourth corresponding area so that the first scanned image m31 may be swapped with the fifth scanned image m35.

Here, the fourth comparative area and the fourth corresponding area may be set to be three-dimensional surface information p31 and p35 of the hard palate. Alternatively, in the first scanned image m31, three-dimensional surface information of a part similar to a position of the three-dimensional surface information m40 of the matching marker displayed in the fifth scanned image m35 is partially deleted (part k31). Also, an edge side of the deleted part may be set to be the fourth comparative area and the fourth corresponding area.

Also, in the CT image m36, the matching marker is imaged and displayed outside imaged three-dimensional data a36 of an alveolar bone of the implantation target portion. Here, since the integrated scanned image m37 is generated by swapping the first scanned image m31 to be replaced with the fifth scanned image m35, the three-dimensional surface information m40 of the matching marker is displayed. Accordingly, when the integrated scanned image m37 is matched with the CT image m36, the three-dimensional surface information and three-dimensional data of the matching marker displayed in respective image data are set to be common parts so that a degree of shape-matching of the image processing process may be significantly improved.

Through the image processing process, in the embodiment, concordance rates between image units of preset comparative areas of the first scanned image m31 and the second scanned image m32 and a corresponding area of the third scanned image m33 are calculated and compared. Here, when the concordance rate is higher than or equal to a preset setting value, the respective scanned images are automatically swapped to be aligned and overlapped, and thus the image processing process may be simplified and a processing period may be significantly reduced.

Here, even when a degree of shape-matching between the first scanned image m31 and the third scanned image m33 is low, they are swapped to be overlapped through the fourth scanned image m34 including all common parts corresponding to the respective images. Accordingly, since three-dimensional surface information of the implantation target portion side that is an edentulous jaw is aligned and disposed at a precise position corresponding to the occlusal vertical dimension, reliability of a three-dimensional planning image finally generated may be significantly improved.

Here, a comparative area and a corresponding area may be more definitely calculated and compared on the basis of the three-dimensional surface information on firm tissue such as the matching tooth, residual teeth, the hard palate, and the like which are displayed in the respective scanned images. Accordingly, since the respective scanned images may be precisely overlapped and deformation of images including design information is substantially minimized, accuracy may be significantly improved.

Here, since the term "comprise," "include," "have," or the like, unless particularly defined otherwise, means that a corresponding component can be included, it should be construed that another component is not excluded and may be further included. All the terms used herein including technical or scientific terms, unless defined otherwise, have the same meanings generally understood by one of ordinary skill in the art. Generally used terms such as the terms defined in dictionaries should be understood as having meanings which coincide with contextual meanings of the related art and will not be understood as ideally or excessively formal meanings unless clearly defined.

As described above, the present invention is not limited to the above-described embodiments and may be modified by one of ordinary skill in the art without departing from the scope of the claims of the present invention and such modifications are included within the scope of the present invention.

INDUSTRIAL APPLICABILITY

The present invention provides a method and a system for manufacturing a dental restoration having improved precision thereof and a general-purpose wax bite applied thereto so as to be applicable to an industrial field of manufacturing dental restorations.

The invention claimed is:

1. A method of manufacturing a dental restoration, comprising:
a first operation of preparing a general-purpose wax bite formed of paraffin wax corresponding to a preset standard dental arch profile, wherein the general-purpose wax bite is configured to be disposed between an implantation target portion and a matching target portion and comprises a variable shape-matching portion corresponding to the implantation target portion and a pressing protrusion integrally formed with the variable shape-matching portion, wherein the variable shape-matching portion is configured to be softened when heated to a temperature higher than or equal to a preset temperature, wherein the pressing protrusion is protruded to correspond to the matching target portion, and is configured to be softened when heated to a temperature higher than or equal to a preset temperature, and wherein the general-purpose wax bite is provided with an interdentium corresponding portion representing an alignment marker configured to be aligned to a preset visible reference indicator formed as an interdentium between residual teeth on any one side of the implantation target portion and the matching target portion;
a second operation of obtaining a plurality of scanned images of the implantation target portion and the matching target portion before and after installation in a state where inner and outer surface portions of the heated general-purpose wax bite are corrected by occlusal pressure in consideration of an occlusal vertical dimension of a person to be treated and a computerized tomography (CT) image of an oral cavity occluded with the general-purpose wax bite through an image capturing device and transmitting the plurality of scanned images and the CT image;
a third operation of generating an integrated scanned image by aligning the plurality of scanned images to correspond to the occlusal vertical dimension while a three-dimensional planning image is generated by overlapping and matching the integrated scanned image with the CT image on the basis of a common part therebetween; and
a fourth operation of generating design information of a dental restoration in consideration of the occlusal vertical dimension on the basis of the three-dimensional planning image while the design information of the dental restoration is transmitted to a manufacturing device so that the dental restoration is manufactured,
wherein in the second operation, the general-purpose wax bite is heated to the temperature higher than or equal to the preset temperature to be softened to have lower strength than the implantation target portion and the matching target portion, and the general-purpose wax bite is pressurized to be shaped in an aligned state using the interdentium corresponding portion so that a distance between the implantation target portion and the matching target portion corresponds to the occlusal vertical dimension,
wherein the variable shape-matching portion having a margin exceeding a width of a standard gingival portion is corrected to correspondingly shape-match with an outer surface profile of the implantation target portion and formed to a shape-matching correction portion and the pressing protrusion is corrected to correspondingly occlude with the matching target portion and formed to an occlusal correction portion, wherein in the second operation, the plurality of scanned images comprise:

a first scanned image of the inner and outer surface portions of the general-purpose wax bite corrected so that an interval from the shape-matching correction portion to the occlusal correction portion corresponds to a preset vertical dimension;

a second scanned image of an outer surface of the matching target portion; and a third scanned image of outer surfaces of the implantation target portion and the matching target portion which are occluded with the general-purpose wax bite, wherein in the third operation, the first scanned image is swapped so that a boundary lines are set along outer edges of three-dimensional surface information of the shape-matching correction portion and three-dimensional surface information of the occlusal correction portion of the general-purpose wax bite; a space between the boundary lines of the three-dimensional surface information of the shape-matching correction portion and the three-dimensional surface information of the occlusal correction portion is set to be a deletion area and deleted; and the boundary line of the three-dimensional surface information of the shape-matching correction portion is exposed to be convex toward the matching target portion.

2. The method of claim 1, wherein in the second operation, the shape-matching correction portion is relined so that an inner surface is filled with a curable resin and occluded and a gap between the shape-matching correction portion and the implantation target portion is compensated for.

3. The method of claim 1, wherein in the second operation, a plurality of matching markers are attached to the outer surface portion of the general-purpose wax bite while the matching markers are displayed as an image in respective pieces of image data comprising an image of the general-purpose wax bite, wherein in the third operation, the first scanned image is swapped so that a boundary line is set between three-dimensional surface information of the shape-matching correction portion in which image data regarding the matching markers is included and three-dimensional surface information of the occlusal correction portion of the general-purpose wax bite while the three-dimensional surface information of the occlusal correction portion is set to be a deletion area and deleted and three-dimensional surface information of the matching markers and the three-dimensional surface information of the shape-matching correction portion of the general-purpose wax bite are exposed, and wherein the integrated scanned image and the CT image are overlapped and matched on the basis of common parts comprising the image data regarding the matching markers displayed therein so that the three-dimensional planning image is generated.

4. The method of claim 1, wherein in the third operation, the integrated scanned image is generated by overlapping and aligning the first scanned image and the second scanned image on the basis of the common part with the third scanned image corresponding to the occlusal vertical dimension while the first scanned image is swapped to externally expose three-dimensional surface information of the shape-matching correction portion corresponding to the inner surface portion of the general-purpose wax bite in consideration of the occlusal vertical dimension.

5. The method of claim 4, wherein in the third operation, in a case that a concordance calculated by comparing a preset comparative area of each of the first scanned image and the second scanned image to a corresponding area of the third scanned image is higher than or equal to a preset setting value, the comparative areas of the first scanned image and the second scanned image are aligned with the corresponding area of the third scanned image to be swapped.

6. The method of claim 1, wherein in the second operation, the first scanned image is obtained by scanning an overall surface of the general-purpose wax bite relined by filling and occluding the shape-matching correction portion with a curable resin and correcting a gap between the shape-matching correction portion and the implantation target portion and corrected by laminating a curable resin on the occlusal correction portion to allow an end side of the matching target portion to be shape-matched and held.

7. The method of claim 1, wherein in the second operation, a plurality of matching markers are attached to an outer surface of the implantation target portion, the matching markers are displayed as an image in each piece of image data comprising an image of the implantation target portion, and a fifth scanned image of the overall outer surface of the implantation target portion to which the matching markers are attached is further obtained, and wherein the third operation further comprises an operation in which when a concordance calculated by comparing a preset fourth comparative area of the fifth scanned image to a fourth corresponding area of the first scanned image is higher than or equal to a preset setting value, the fourth comparative area is aligned with the fourth corresponding area so that the first scanned image is swapped with the fifth scanned image.

8. The method of claim 1, wherein the fourth operation further comprises an operation of generating design information of a surgical guide comprising a fixing groove portion shape-matched with the implantation target portion and a guide hole formed along an implantation position of a fixture for fixing the dental restoration to the implantation target portion and the design information of the surgical guide is transmitted to a manufacturing device so that the surgical guide is manufactured.

* * * * *